(12) United States Patent
Manicka et al.

(10) Patent No.: US 8,795,174 B2
(45) Date of Patent: Aug. 5, 2014

(54) ADHERENT DEVICE WITH MULTIPLE PHYSIOLOGICAL SENSORS

(75) Inventors: Yatheendhar D. Manicka, Woodbury, MN (US); Badri Amurthur, Los Gatos, CA (US); Mark J. Bly, Falcon Heights, MN (US); Kristofer J. James, Eagan, MN (US); Imad Libbus, Saint Paul, MN (US); Scott T. Mazar, Woodbury, MN (US); Jerry S. Wang, Blaine, MN (US)

(73) Assignee: Corventis, Inc., San Jose, CA (US)

( * ) Notice: Subject to any disclaimer, the term of this patent is extended or adjusted under 35 U.S.C. 154(b) by 0 days.

(21) Appl. No.: 13/598,238

(22) Filed: Aug. 29, 2012

(65) Prior Publication Data

US 2013/0085347 A1 Apr. 4, 2013

Related U.S. Application Data

(62) Division of application No. 12/209,288, filed on Sep. 12, 2008, now abandoned.

(60) Provisional application No. 60/972,537, filed on Sep. 14, 2007, provisional application No. 60/972,629, filed on Sep. 14, 2007, provisional application No. 61/055,666, filed on May 23, 2008, provisional application No. 61/055,645, filed on May 23, 2008.

(51) Int. Cl.
*A61B 5/00* (2006.01)
*G06F 19/00* (2011.01)
*A61B 5/053* (2006.01)

(52) U.S. Cl.
CPC .......... *G06F 19/3431* (2013.01); *A61B 5/0535* (2013.01); *A61B 5/4875* (2013.01); *A61B 5/6801* (2013.01); *A61B 5/6833* (2013.01); *A61B 5/746* (2013.01); *G06F 19/3418* (2013.01); *A61B 5/0537* (2013.01)
USPC ............ 600/301; 600/547; 600/391; 600/392

(58) Field of Classification Search
None
See application file for complete search history.

(56) References Cited

U.S. PATENT DOCUMENTS

| | | | |
|---|---|---|---|
| 3,584,618 A | 6/1971 | Reinhard et al. | |
| 5,713,367 A * | 2/1998 | Arnold et al. | 600/517 |
| 6,453,186 B1 | 9/2002 | Lovejoy et al. | |
| 6,577,897 B1 | 6/2003 | Shurubura et al. | |
| 2002/0019586 A1 | 2/2002 | Teller et al. | |
| 2002/0022786 A1 | 2/2002 | Takehara et al. | |
| 2002/0099283 A1* | 7/2002 | Christ et al. | 600/369 |
| 2002/0143265 A1* | 10/2002 | Ackerman et al. | 600/515 |
| 2004/0122295 A1* | 6/2004 | Hatlestad et al. | 600/300 |
| 2004/0122489 A1 | 6/2004 | Mazar et al. | |
| 2005/0261743 A1* | 11/2005 | Kroll | 607/8 |
| 2006/0030781 A1* | 2/2006 | Shennib | 600/509 |
| 2006/0030782 A1* | 2/2006 | Shennib | 600/509 |

(Continued)

*Primary Examiner* — Gary Jackson
*Assistant Examiner* — Davin K Sands
(74) *Attorney, Agent, or Firm* — Kilpatrick Townsend & Stockton LLP

(57) ABSTRACT

An adherent device to monitor a patient comprises an adhesive patch to adhere to a skin of the patient. At least four electrodes are connected to the patch and capable of electrically coupling to the patient. Impedance circuitry is coupled to the at least four electrodes to measure a hydration signal of the patient. Electrocardiogram circuitry is coupled to at least two of the at least four electrodes to measure an electrocardiogram signal of the patient. An accelerometer can be mechanically coupled to the adhesive patch to generate a signal in response to at least one of an activity or a position of the patient.

26 Claims, 17 Drawing Sheets

(56) References Cited

U.S. PATENT DOCUMENTS

| | | | |
|---|---|---|---|
| 2006/0064030 A1* | 3/2006 | Cosentino et al. | 600/547 |
| 2006/0167374 A1 | 7/2006 | Takehara et al. | |
| 2007/0033072 A1* | 2/2007 | Bildirici | 705/3 |
| 2007/0043394 A1* | 2/2007 | Zhang et al. | 607/8 |
| 2007/0073169 A1* | 3/2007 | Averina et al. | 600/483 |
| 2007/0208232 A1 | 9/2007 | Kovacs | |
| 2007/0265533 A1* | 11/2007 | Tran | 600/481 |
| 2008/0001735 A1* | 1/2008 | Tran | 340/539.22 |
| 2009/0105555 A1* | 4/2009 | Dacso et al. | 600/301 |
| 2010/0063365 A1* | 3/2010 | Pisani et al. | 600/301 |

\* cited by examiner

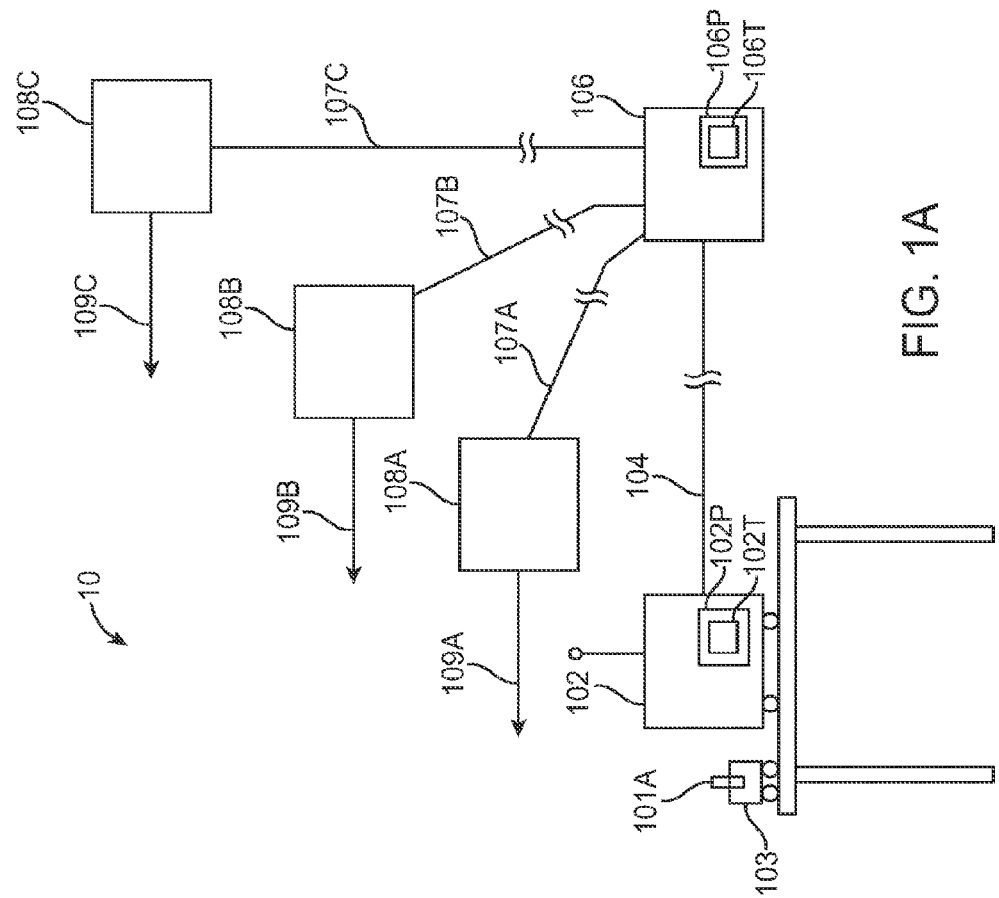
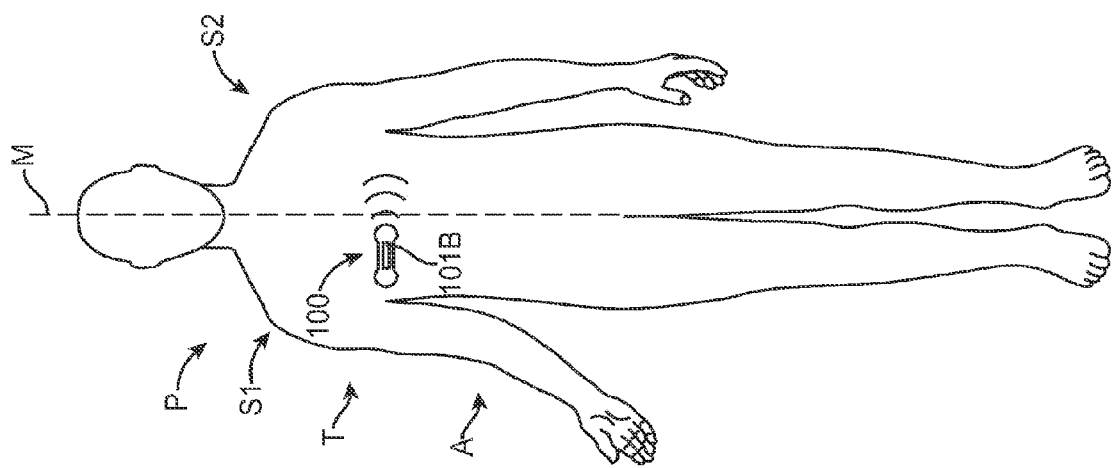
FIG. 1A

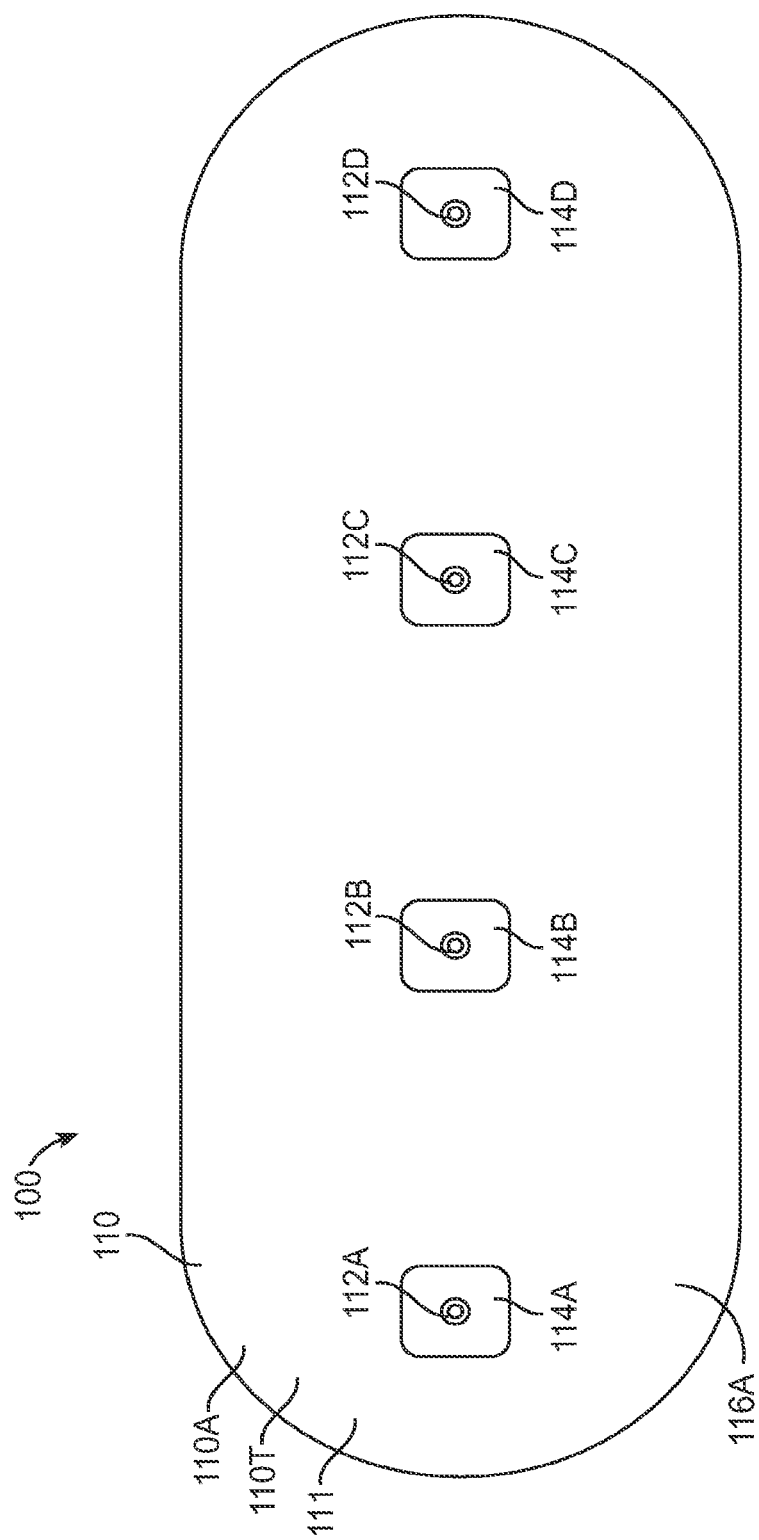

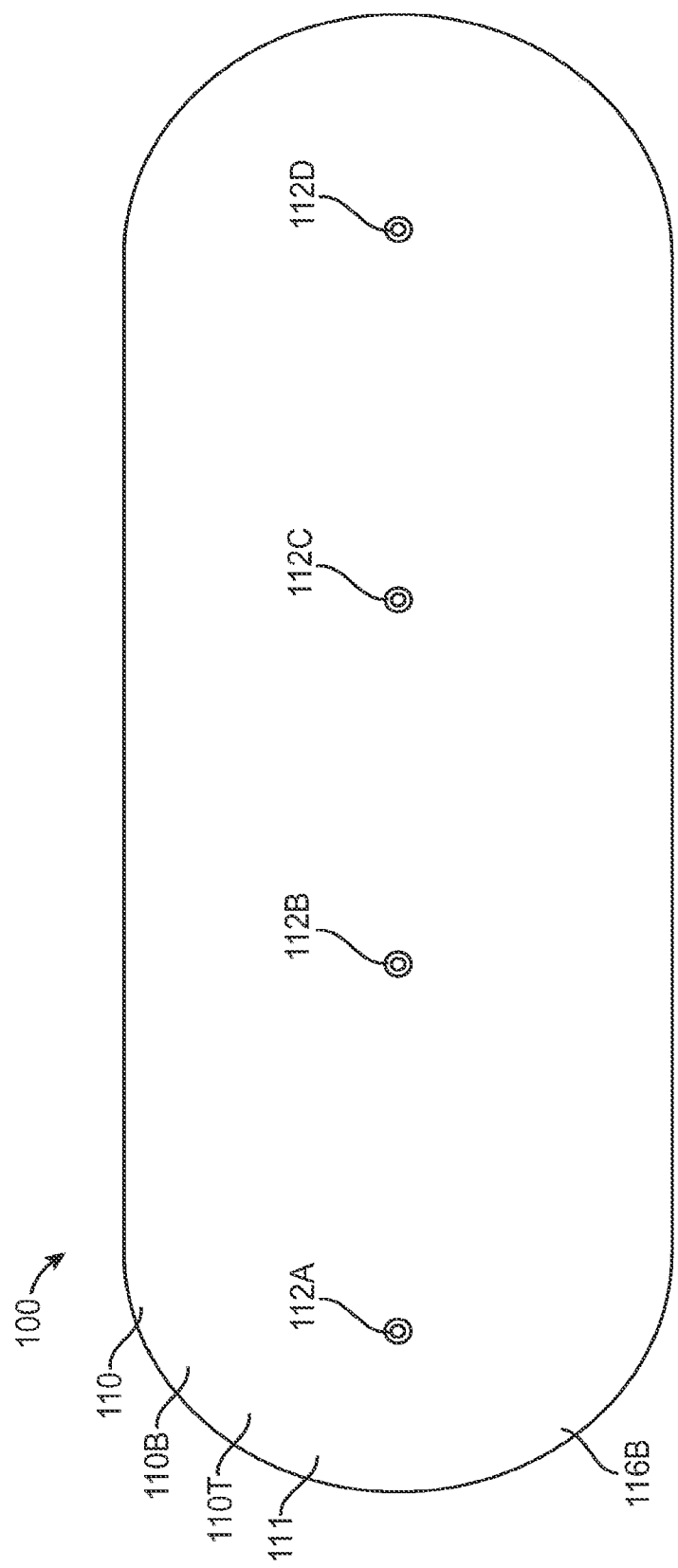

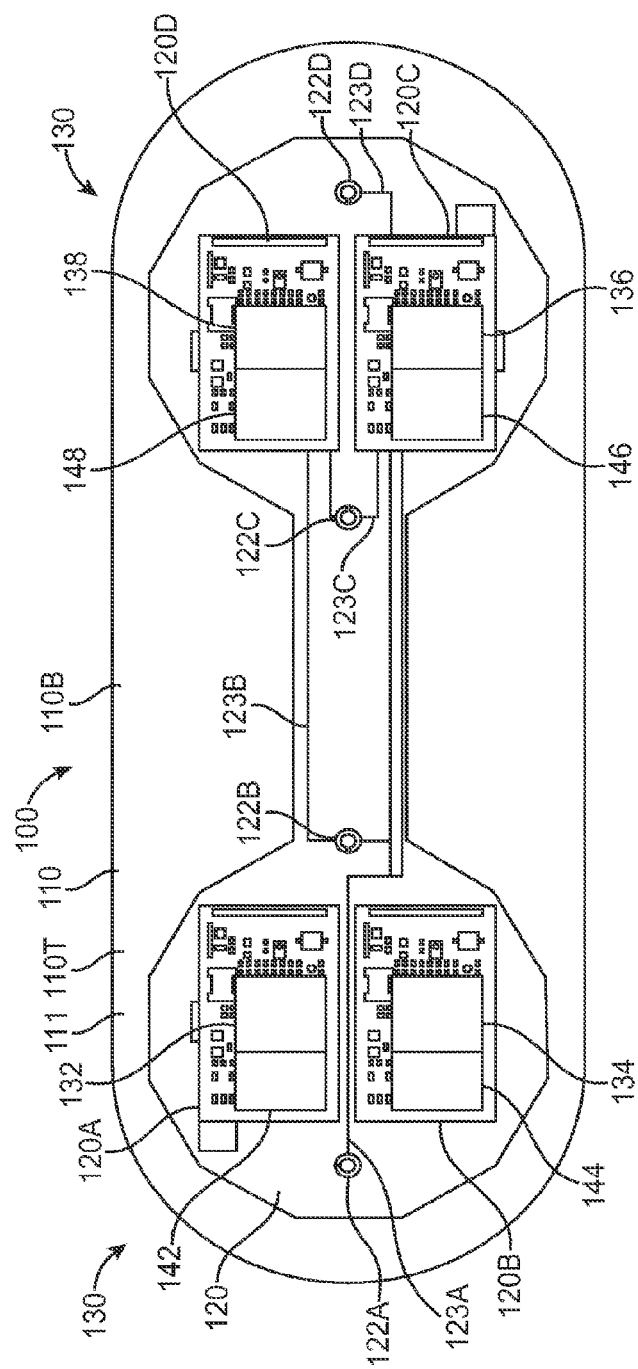
FIG. 1D
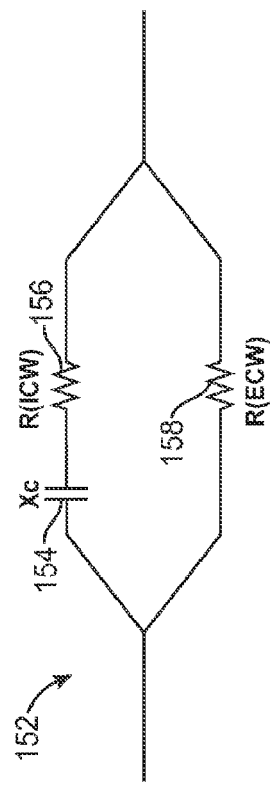
FIG. 1D1

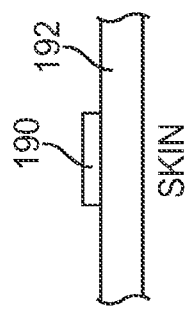
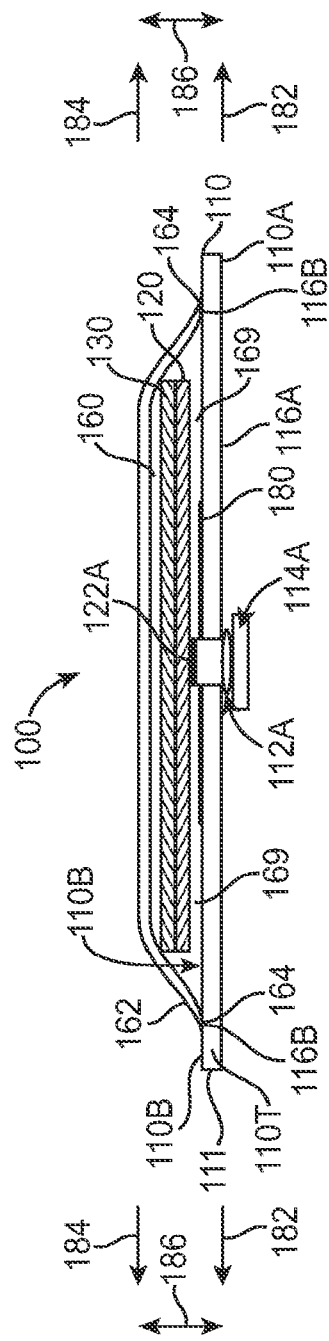

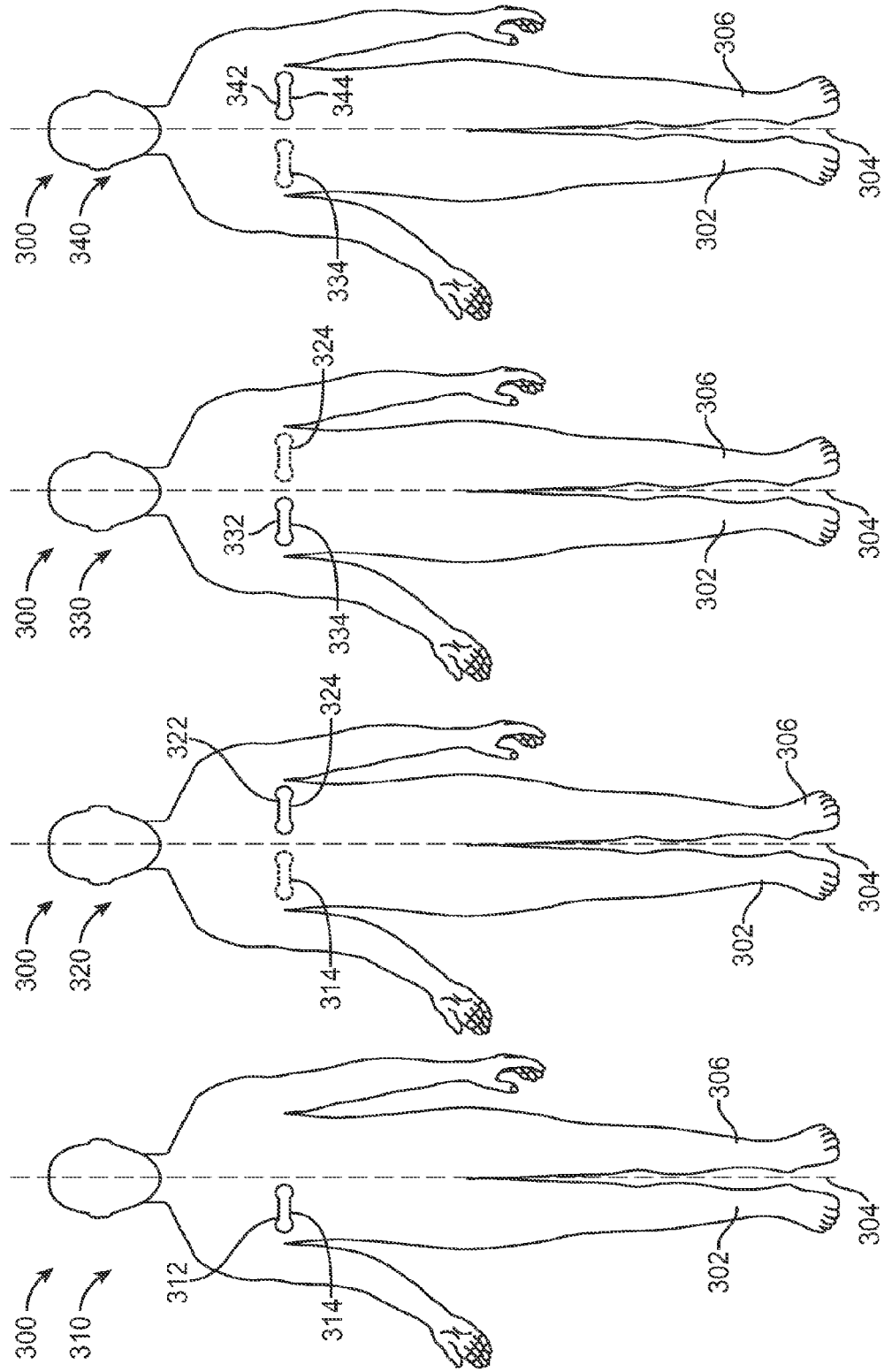

ADHERENT DEVICE WITH MULTIPLE PHYSIOLOGICAL SENSORS

CROSS-REFERENCES TO RELATED APPLICATIONS

The present application is a divisional application of U.S. patent application Ser. No. 12/209,288 filed on Sep. 12, 2008, which claims the benefit under 35 USC 119(e) of U.S. Provisional Application No. 60/972,537 and 60/972,629 both filed Sep. 14, 2007, and 61/055,645 and 61/055,666 both filed May 23, 2008; the full disclosures of which are incorporated herein by reference in their entirety.

The subject matter of the present application is related to the following applications: Nos. 60/972,512; 60/972,329; 60/972,354; 60/972,616; 60/972,363; 60/972,343; 60/972,581; 60/972,316; 60/972,333; 60/972,359; 60/972,336; 60/972,340 all of which were filed on Sep. 14, 2007; 61/046,196 filed Apr. 18, 2008; 61/047,875 filed Apr. 25, 2008; 61/055,656 and 61/055,662 both filed May 23, 2008; and 61/079,746 filed Jul. 10, 2008.

The following applications are being filed concurrently with the present application, on Sep. 12, 2008: U.S. patent application Ser. No. 12/209,279 entitled "Multi-Sensor Patient Monitor to Detect Impending Cardiac Decompensation"; U.S. patent application Ser. No. 12/209,430 entitled "Injectable Device for Physiological Monitoring"; U.S. patent application Ser. No. 12/209,479 entitled "Injectable Physiological Monitoring System"; U.S. patent application Ser. No. 12/209,262 entitled "Adherent Device for Cardiac Rhythm Management"; U.S. patent application Ser. No. 12/209,268 entitled "Adherent Device for Respiratory Monitoring"; U.S. patent application Ser. No. 12/209,269 entitled "Adherent Athletic Monitor"; U.S. patent application Ser. No. 12/209,259 entitled "Adherent Emergency Monitor"; U.S. patent application Ser. No. 12/209,273 entitled "Adherent Device with Physiological Sensors"; U.S. patent application Ser. No. 12/209,276 entitled "Medical Device Automatic Start-up upon Contact to Patient Tissue"; U.S. patent application Ser. No. 12/210,078 entitled "System and Methods for Wireless Body Fluid Monitoring"; U.S. patent application Ser. No. 12/209,265 entitled "Adherent Cardiac Monitor with Advanced Sensing Capabilities"; U.S. patent application Ser. No. 12/209,292 entitled "Adherent Device for Sleep Disordered Breathing"; U.S. patent application Ser. No. 12/209,278 entitled "Dynamic Pairing of Patients to Data Collection Gateways"; U.S. patent application Ser. No. 12/209,508 entitled "Adherent Multi-Sensor Device with Implantable Device Communications Capabilities"; U.S. patent application Ser. No. 12/209,528 entitled "Data Collection in a Multi-Sensor Patient Monitor"; U.S. patent application Ser. No. 12/209,271 entitled "Adherent Multi-Sensor Device with Empathic Monitoring"; U.S. patent application Ser. No. 12/209,274 entitled "Energy Management for Adherent Patient Monitor"; and U.S. patent application Ser. No. 12/209,294 entitled "Tracking and Security for Adherent Patient Monitor."

BACKGROUND OF THE INVENTION

1. Field of the Invention

The present invention relates to patient monitoring. Although embodiments make specific reference to monitoring impedance and electrocardiogram signals with an adherent patch, the system methods and device described herein may be applicable to many applications in which physiological monitoring is used, for example wireless physiological monitoring for extended periods.

Patients are often treated for diseases and/or conditions associated with a compromised status of the patient, for example a compromised physiologic status. In some instances, a patient may report symptoms that require diagnosis to determine the underlying cause. For example, a patient may report fainting or dizziness that requires diagnosis, in which long term monitoring of the patient can provide useful information as to the physiologic status of the patient. In some instances a patient may have suffered a heart attack and require care and/or monitoring after release from the hospital. One example of a device to provide long term monitoring of a patient is the Holter monitor, or ambulatory electrocardiography device.

In addition to measuring heart signals with electrocardiograms, known physiologic measurements include impedance measurements. For example, transthoracic impedance measurements can be used to measure hydration and respiration. Although transthoracic measurements can be useful, such measurements may use electrodes that are positioned across the midline of the patient, and may be somewhat uncomfortable and/or cumbersome for the patient to wear.

Work in relation to embodiments of the present invention suggests that known methods and apparatus for long term monitoring of patients may be less than ideal. At least some of the known devices may not collect the right kinds of data to treat patients optimally. For example, although successful at detecting and storing electrocardiogram signals, devices such as the Holter monitor can be somewhat bulky and may not collect all of the kinds of data that would be ideal to diagnose and/or treat a patient. In at least some instances, devices that are worn by the patient may be somewhat uncomfortable, which may lead to patients not wearing the devices and not complying with direction from the health care provider, such that data collected may be less than ideal. Although implantable devices may be used in some instances, many of these devices can be invasive and/or costly, and may suffer at least some of the shortcomings of known wearable devices.

Therefore, a need exists for improved patient monitoring. Ideally, such improved patient monitoring would avoid at least some of the short-comings of the present methods and devices.

2. Description of Background Art

The following U.S. Patents and Publications may describe relevant background art: U.S. Pat. Nos. 3,370,459; 3,805,769; 3,845,757; 3,972,329; 4,121,573; 4,141,366; 4,838,273; 4,955,381; 4,981,139; 5,080,099; 5,353,793; 5,511,553; 5,544,661; 5,558,638; 5,724,025; 5,772,586; 5,862,802; 6,047,203; 6,117,077; 6,129,744; 6,225,901; 6,385,473; 6,416,471; 6,454,707; 6,527,711; 6,527,729; 6,551,252; 6,595,927; 6,595,929; 6,605,038; 6,645,153; 6,795,722; 6,821,249; 6,980,851; 7,020,508; 7,054,679; 7,153,262; 2003/0092975; 2005/0113703; 2005/0131288; 2006/0010090; 2006/0031102; 2006/0089679; 2006/0155183; 2006/122474; 2006/0224051; 2006/0264730; 2007/0021678; and 2007/0038038.

BRIEF SUMMARY OF THE INVENTION

The present invention relates to patient monitoring. Although embodiments make specific reference to monitoring impedance and electrocardiogram signals with an adherent patch, the system methods and device described herein may be applicable to any application in which physiological monitoring is used, for example wireless physiological monitoring for extended periods.

In a first aspect, embodiments of the present invention provide an adherent device to monitor a patient. The device comprises an adhesive patch to adhere to a skin of the patient. At least four electrodes are connected to the patch and capable of electrically coupling to the patient. Impedance circuitry can be coupled to the at least four electrodes to measure a hydration signal of the patient. Electrocardiogram circuitry can be coupled to at least two of the at least four electrodes to measure an electrocardiogram signal of the patient. An accelerometer can be mechanically coupled, for exampled adhered or affixed, to the adhesive patch to generate an accelerometer signal in response to at least one of an activity or a position of the patient. Work in relation to embodiments of the present invention suggests accelerometer signals can improve patient diagnosis, and can be especially useful when used with other signals, such as electrocardiogram signals and impedance signals for hydration and respiration. Mechanically coupling the accelerometer to the electrodes for measuring impedance and hydration may also improve the quality and/or usefulness of the impedance and/or electrocardiogram signals. For example, mechanical coupling of the accelerometer to the electrodes and to the skin of the patient can improve the reliability, quality and/or accuracy of the accelerometer measurements, as the electrode signals can indicate the quality of mechanical coupling of the patch to the patient so as to indicate that the device is connected to the patient and that the accelerometer signals are valid. In some embodiments, the adherent device may comprise a dimension across that is no more than about 8 inches, such that the device can be comfortably worn by at least some patients for an extended period to permit collection of the electrocardiogram, impedance and accelerometer signals for extended periods.

In many embodiments, the adhesive patch is mechanically coupled to the at least four electrodes, the impedance circuitry, the electrocardiogram circuitry and the accelerometer, such that the patch is capable of supporting the at least four electrodes, the impedance circuitry, the electrocardiogram circuitry and the accelerometer when the adherent patch is adhered to the skin of the patient.

In many embodiments, a wireless communication circuitry is coupled to the impedance circuitry, the electrocardiogram circuitry and the accelerometer to transmit to a remote center with a communication protocol at least one of the hydration signal, the electrocardiogram signal or the accelerometer signal. The wireless communication circuitry can be configured to transmit the hydration signal, the electrocardiogram signal and the accelerometer signal to the remote center with a single wireless hop from the wireless communication circuitry to an intermediate device. In specific embodiments, the communication protocol can comprise at least one of Bluetooth, Zigbee, WiFi, WiMax, IR, a cellular protocol, amplitude modulation or frequency modulation. In many embodiments, the intermediate device comprises a data collection system to collect and/or store data from the wireless transmitter, and the data collection system can be configured to communicate periodically with the remote center with wireless communication and/or wired communication. The communications protocol may comprise a two way protocol such that the remote center is capable of issuing commands to control data collection The adherent device may comprise many sensors configured to measure many different signals. In many embodiments, the accelerometer comprises at least one of a piezoelectric accelerometer, capacitive accelerometer or electromechanical accelerometer and wherein the accelerometer comprises a 3-axis accelerometer to measure at least one of an inclination, a position, an orientation or acceleration of the patient in three dimensions. The impedance circuitry can be adapted to measure extracellular fluid of the patient with at least one frequency within a range from about 0.5 kHz to about 200 kHz., and the impedance circuitry is configured to determine a respiration of the patient. The device may comprise a microphone to detect an audio signal from within the patient, and the audio signal may comprise a heart sound with an S3 heart sound and/or a respiratory sound with rales and/or crackles. The device may comprise a temperature sensor to measure a temperature of the patient. Work in relation to embodiments of the present invention suggest that patient temperature may effect impedance measurements, such that the impedance measurements can be corrected with the temperature measurement.

In many embodiments, the adherent device comprises a processor comprising a tangible medium, and the processor is configured to control a collection and transmission of data from the impedance circuitry, the electrocardiogram circuitry and the accelerometer. The adherent device may comprise a real time clock and a frequency generator.

In another aspect, embodiments of the present invention provide a method of monitoring a patient. An adhesive patch is adhered to a skin of the patient to couple at least four electrodes to the skin of the patient. A hydration signal of the patient is measured with impedance circuitry coupled to the at least four electrodes. An electrocardiogram signal of the patient is measured with electrocardiogram circuitry coupled to at least two of the at least four electrodes. A signal from an accelerometer is measured in response to at least one of an activity or a position of the patient.

In many embodiments, the adhesive patch supports the at least four electrodes, the impedance circuitry, the electrocardiogram circuitry and the accelerometer when the adherent patch is adhered to the skin of the patient.

In another aspect, embodiments of the present invention provide an adherent device to monitor a patient. The adherent device comprises an adhesive patch to adhere to a skin of the patient. At least four electrodes are affixed to the patch and capable of electrically coupling to the patient. A maximum dimension across the at least 4 electrodes may comprise no more that about eight inches, such that the at least four electrodes are capable of adhering to either a left side or a right side of the patient. Impedance circuitry may be coupled to the at least four electrodes to measure hydration of the patient. Electrocardiogram circuitry may be coupled to at least two of the at least four electrodes to measure an electrocardiogram of the patient.

In many embodiments, the maximum distance across the at least four electrodes comprises no more than about six inches. The device comprises a maximum dimension across no more than about 8 inches, and the patch is capable of measuring the electrocardiogram and the impedance from a left side or a right side of the patient.

In another aspect, an adherent device to monitor a patient for an extended period is provided. The device comprises a breathable tape comprising an adhesive coating to adhere the breathable tape to a skin of the patient, such that tape and device may be comfortable when worn by the patient. The breathable tape may comprise a porous material, for example a porous fabric, to allow transmission of water vapor while the device is worn by the patient. At least one electrode is affixed to the breathable tape and capable of electrically coupling to a skin of the patient. At least one gel can be disposed over a contact surface of the at least one electrode to electrically connect the electrode to the skin. A printed circuit board, for example, a flex printed circuit board, can be connected to the breathable tape to support the printed circuit board with the breathable tape when the tape is adhered to the patient. Electronic components may be electrically connected to the printed circuit board and coupled to the at least one electrode to measure physiologic signals of the patient. A breathable cover, which may be water resistant, can be disposed over the circuit board and electronic components and connected to at least one of the electronics components, the printed circuit board or the breathable tape.

In many embodiments, an electronics housing is adhered to at least one of the electronics circuitry or the printed circuit board, such that the electronics housing is disposed between the cover and the electronics components.

In many embodiments, a gel cover is positioned over a breathable tape to inhibit a flow of the gel through the breathable tape. The printed circuit board, for example a flex printed circuit board, may be located over the gel cover such that the gel cover is disposed between the breathable tape and the printed circuit board.

In many embodiments, the breathable tape comprises a first porosity, and the gel cover comprises a breathable tape with a second porosity, in which the second porosity is less than the first porosity to inhibit flow of the gel through the breathable tape. In specific embodiments, the breathable tape comprises a tricot-knit polyester fabric backing with an acrylate adhesive coating, and the gel cover comprises a polyurethane, non-woven backing with an acrylate adhesive coating.

In many embodiments, the breathable tape, the adhesive coating, the at least one electrode and gel coating are separable from the printed circuit board, electronic components, and water resistant housing and cover, such that the printed circuit board, electronic components, water resistant housing and water proof cover are reusable.

In many embodiments, the at least one electrode extends through at least one aperture in the breathable tape. In some embodiments, the at least one electrode is configured to electrically couple to the printed circuit board through the breathable tape.

In another aspect, embodiments of the present invention provide a method of monitoring a patient for an extended period. An electronics module is attached to a first adherent patch component of a plurality of adherent patch components. The first adherent patch component is adhered to a skin of the patient. The electronics module is removed from the first adherent patch component. The electronics module is attached to a second patch component of the plurality of patch components after the first adherent patch component has been removed.

In many embodiments, the electronics module is removed from the second adherent patch component, and the electronics module is attached to a third patch component of the plurality of patch components after the second adherent patch component has been removed.

In many embodiments, impedance signals are measured when the third adherent patch component is adhered to the patient.

In another aspect, embodiments of the present invention provide a system to monitor a patient for an extended period. The system comprise a plurality of adherent patch components. An electronics module may be adapted to couple to each of the plurality of patch components for sequential measurements from each of the patch components.

In many embodiments, each of the plurality of adherent patch components comprises, a breathable tape with an adhesive coating to adhere the breathable tape to a skin of the patient, and at least one electrode affixed to the breathable tape.

In many embodiments, the electronics module comprises a printed circuit board configured to connect electrically to the at least one electrode to measure physiologic signals of the patient, electronic components electrically connected to the printed circuit board, and a housing adhered to at least one of the electronics module or the printed circuit board.

In another aspect, embodiments of the present invention provide a method of monitoring a patient for an extended period of time. A first adherent patch is adhered on a first side of the patient, in which the first adherent patch comprises first electrodes to measure at least one of an electrocardiogram or an impedance. The at least one of the electrocardiogram or the impedance is measured from the first side of the patient for a first period of time. The first patch is removed from the first side of the patient. A second adherent patch is placed on a second side of the patient, in which the second adherent patch comprises second electrodes to measure the at least one of the electrocardiogram or the impedance. The at least one of the electrocardiogram or the impedance is measured from the second side of the patient for a second period of time after the first patch has been removed.

In many embodiments, the first side comprises at least one of a left side or a right side of the patient, and the second side is opposite the first side.

In many embodiments, the second patch is removed from the second side of the patient, and a third adherent patch is placed on the first side of the patient, in which the third patch comprises third electrodes to measure the at least one of the electrocardiogram or the impedance. The at least one of the electrocardiogram or the impedance is measured from the first side of the patient for a third period of time after the second patch has been removed.

In many embodiments, the third patch is removed from the first side of the patient. A fourth adherent patch is placed on the second side of the patient, in which the fourth patch comprising fourth electrodes to measure the at least one of the electrocardiogram or the impedance. The at least one of the electrocardiogram or the impedance is measured from the second side of the patient for a fourth period of time after the third patch has been removed.

In specific embodiments, each of the first period of time, the second period of time, the third period of time and the fourth period of time comprises at least about 1 week.

In another aspect, embodiments of the present invention provide a method of monitoring a patient for an extended period of time. A first adherent patch is placed on a skin location on a first side of the patient, in which the first adherent patch comprises first electrodes to measure at least one of an electrocardiogram or an impedance. The at least one of the electrocardiogram or the impedance is measured from the first adherent patch on the first skin location for a first period of time. The first patch is removed from the first skin location. A second adherent patch is placed on a second skin location on a second side of the patient, in which the second adherent patch comprises second electrodes to measure the at least one of the electrocardiogram or the impedance. The at least one of the electrocardiogram or the impedance is measured from the second skin location for a second period of time after the first patch has been removed.

In many embodiments, the first skin location heals during the second period of time.

In another aspect, embodiments of the present invention provide an adherent device to monitor a patient. The device comprises an adhesive patch to adhere to a skin of the patient. At least four electrodes are mechanically coupled to the patch and capable of electrically coupling to the patient. The at least four electrodes may comprise at least two force electrodes and at least two sense electrodes. Impedance circuitry may be electrically coupled to the at least two force electrodes to force an electrical current and to the at least two sense electrodes to measure a hydration signal of the patient. Electrocardiogram circuitry can be coupled to the at least two force electrodes to measure an electrocardiogram signal of the patient.

In many embodiments, the adherent device comprises electrical switches connected to the at least two force electrodes to isolate the at least two force electrodes from the impedance circuitry when the electrocardiogram circuitry measures the electrocardiogram. In specific embodiments, a processor an be configured to control the impedance circuitry and the electrocardiogram circuitry so as to time division multiplex collection the hydration signal and the electrocardiogram signal. The processor may be configured to decouple the at least two force electrodes from the impedance circuitry when the electrocardiogram circuitry measures the electrocardiogram signal.

In many embodiments, the at least four electrodes comprise no more than four electrodes.

In some embodiments, the at least two force electrodes comprise outer electrodes and the at least two sense electrodes comprise inner electrodes.

In some embodiments, the at least two force electrodes comprise inner electrodes and the at least two sense electrodes comprise outer electrodes.

In another aspect, embodiments of the present invention provide a method of monitoring a patient. An adhesive patch is adhered to a skin of the patient so as to couple at least four electrodes to the skin of the patient, in which the at least four electrodes comprise at least two force electrodes and at least two sense electrodes. A hydration signal of the patient is measured with impedance circuitry electrically coupled to the at least two force electrodes and to the at least two sense electrodes, such that the at least two force electrodes force an electrical current between the at least two force electrodes. An electrocardiogram signal of the patient is measured with electrocardiogram circuitry coupled to the at least two force electrodes.

In many embodiments, electrical switches connected to the at least two force electrodes can be opened to isolate the at least two force electrodes from the impedance circuitry when the electrocardiogram circuitry measures the electrocardiogram.

In many embodiments, the hydration signal and the electrocardiogram signal can be time division multiplexed.

In another aspect, embodiments of the present inventions provide an adherent device to monitor a patient. The device comprises an adhesive patch and at least two electrodes connected to the patch. The device also comprises circuitry coupled to at least two electrodes to measure at least two of an electrocardiogram signal, a respiration signal of the patient or an activity signal of the patient, and a processor system. The adhesive patch can adhere to a skin of the patient. The electrodes are capable of electrically coupling to the patient. The processor system comprises a tangible medium configured to trigger an alarm in response to the at least two of the electrocardiogram signal, the respiration signal or the activity signal.

In many embodiments, the processor system comprises a first processor and a second processor. The first processor may comprise a tangible medium attached to the adherent patch. The second processor may comprise a tangible medium at a remote center.

In many embodiments, the processor system is configured to combine at least two of the electrocardiogram signal, the respiration signal or the activity signal, the purpose of which may be to detect an impending cardiac decompensation. Combining may comprise at least one of adding, subtracting, multiplying, scaling, or dividing the at least two of the electrocardiogram signal, the hydration signal, the respiration signal, or the activity signal. In some embodiments, the at least two of the electrocardiogram signal, the respiration signal, or the activity signal can be combined with at least one of a weighted combination, a tiered combination, or a logic gated combination, a time weighted combination or a rate of change.

In many embodiments, the processor system is configured to continuously monitor, store in tangible media, and transmit to a remote center at least two of the electrocardiogram signal, the respiration signal or the activity signal when the alarm is triggered.

In many embodiments, the processor system is configured to trigger the alarm and alert the patient and/or the physician in response to an adverse cardiac event.

In many embodiments, the processor system is configured to calculate and report a patient risk of sudden cardiac death to at least one of a remote center or a physician.

In many embodiments, the processor system is configured to detect at least one of a T-wave alternans, a pulsus alternans, an autonomic imbalance, a heart rate variability in response to at least two of the electrocardiogram signal, the respiration signal or the activity signal.

In many embodiments, the processor system is configured to loop record at least two of the electrocardiogram signal, the respiration signal or the activity signal for diagnosis of an unexplained syncope and/or arrhythmia when the alarm is triggered.

In many embodiments, the processor system is configured to detect an event comprising at least one of an atrial fibrillation in response to the electrocardiogram signal or an acute myocardial infarction in response to an ST segment elevation of the electrocardiogram signal.

In many embodiments, the processor system is configured to monitor a high risk patient post myocardial infarction with at least two of the electrocardiogram signal, the respiration signal or the activity signal.

In many embodiments, the processor system is configured to continuously monitor a bradycardia of the patient at risk for sudden death, the electrocardiogram signal comprising at least one of a Brugada Syndrome with an ST elevation and a short QT interval or long-QT interval.

In many embodiments, the processor system is configured to monitor the electrocardiogram signal and an alert at least one of a patient, a remote center a physician, emergency responder, or family/caregiver in response to an adverse event.

In many embodiments, the processor system is configured to determine a tiered response to at least two of the electrocardiogram signal, the respiration signal or the activity signal.

In some embodiments, the tiered response may comprise a first tier to contact an emergency responder in response to an immediate life threatening event, a second tier to contact a physician in response to an event that requires medical care, a third tier to contact a family member and/or care giver, and a fourth tier to contact the center.

In some embodiments, the immediate life threatening event comprises at least one of a sustained ventricular tachycardia, a sustained ventricular fibrillation, an asystole, an arrhythmia with no respiration or an arrhythmia with no patient movement.

In some embodiments, the event that requires medical care comprises an atrial fibrillation that is not immediately life threatening.

In some embodiments, the wireless communication circuitry is configured to transmit at least two of the electrocardiogram signal, the respiration signal or the activity signal with a single wireless hop from the wireless communication circuitry to an intermediate device.

In another aspect, embodiments of the present invention provides a method of monitoring a patient. An adhesive patch is adhered to a skin of the patient so as to couple at least two electrodes to the skin of the patient. Circuitry coupled to the at least two electrodes measures at least two of an electrocardiogram signal of the patient, a respiration signal of the patient or an activity signal of the patient. An alarm may be triggered by a processor system in response to the at least two of the electrocardiogram signal, the respiration signal or the activity signal with the processor system comprising a tangible medium.

In many embodiments, the processor system comprises a first processor and a second processor. The first processor comprises a tangible medium attached to the adherent patch and the second processor comprises a tangible medium at a remote center.

In many embodiments, at least two of the electrocardiogram signal, the respiration signal, or the activity signal are combined, which may be to detect am impending cardiac decompensation. In some embodiments, combining may comprise at least one of adding, subtracting, multiplying, scaling or dividing the at least two of the electrocardiogram signal, the hydration signal, the respiration signal or the activity signal. In some embodiments, the at least two of the electrocardiogram signal, the respiration signal, or the activity signal can be combined with at least one of a weighted combination, a tiered combination, or a logic gated combination, a time weighted combination or a rate of change.

In many embodiments, at least two of the electrocardiogram signal, the respiration signal, or the activity signal are continuously monitored, stored, and/or transmitted to a remote center.

In many embodiments, the alarm is triggered and the patient and/or the physician is alerted in response to an adverse cardiac event.

In many embodiments, a patient risk of sudden cardiac death is calculated and/or reported to at least one of a remote center or a physician.

In many embodiments, at least one of a T-wave alternans, a pulsus alternans, an autonomic imbalance, a heart rate variability in response to the at least two of the electrocardiogram signal, the respiration signal or the activity signal is detected.

In many embodiments, the at least two of the electrocardiogram signal, the respiration signal or the activity signal is loop recorded when the alarm is triggered.

In many embodiments, an event comprising at least one of an atrial fibrillation in response to the electrocardiogram signal or an acute myocardial infarction in response to an ST segment elevation of the electrocardiogram signal is detected.

In many embodiments, a high risk patent post myocardial infarction is monitored with the at least two of the electrocardiogram signal, the respiration signal or the activity signal.

In many embodiments, a bradycardia of the patient at risk for sudden death, the electrocardiogram signal comprising at least one of a Brugada Syndrome with an ST elevation and a short QT interval or long-QT interval are continuously monitored.

In many embodiments, the electrocardiogram signal is monitored and/or at least one of a patient, a remote center, a physician, emergency responder, or family/caregiver is alerted in response to an adverse event.

In many embodiments, a tiered response to the at least two of the electrocardiogram signal, the respiration signal or the activity signal is determined.

In many embodiments, the tiered response comprises a first tier to contact an emergency responder in response to an immediate life threatening event, a second tier to contact a physician in response to an event that requires medical care, a third tier to contact a family member and/or care giver, and a fourth tier to contact the center.

In many embodiments, the immediate life threatening event comprises at least one of a sustained ventricular tachycardia, a sustained ventricular fibrillation, an asystole, an arrhythmia with no respiration or an arrhythmia with no patient movement.

In many embodiments, the event that requires medical care comprises an atrial fibrillation that is not immediately life threatening.

In some embodiments, wireless communication circuitry transmits the at least two of the electrocardiogram signal, the respiration signal or the activity signal with a single wireless hop from the wireless communication circuitry to an intermediate device.

BRIEF DESCRIPTION OF THE DRAWINGS

FIG. 1A shows a patient and a monitoring system comprising an adherent device, according to embodiments of the present invention;

FIG. 1B shows a bottom view of the adherent device as in FIG. 1A comprising an adherent patch;

FIG. 1C shows a top view of the adherent patch, as in FIG. 1B;

FIG. 1D shows a printed circuit boards and electronic components over the adherent patch, as in FIG. 1C;

FIG. 1D1 shows an equivalent circuit that can be used to determine optimal frequencies for determining patient hydration, according to embodiments of the present invention;

FIGS. 1I and 1J show a side cross-sectional view and an exploded view, respectively, of the adherent device as in FIGS. 1A to 1H;

FIG. 1K shows at least one electrode configured to electrically couple to a skin of the patient through a breathable tape, according to embodiments of the present invention;

FIGS. 3A to 3D show a method of monitoring a patient for an extended period with an adherent patch with adherent patches alternatively adhered to the right side or the left side of the patient;

DETAILED DESCRIPTION OF THE INVENTION

Figure 1E:
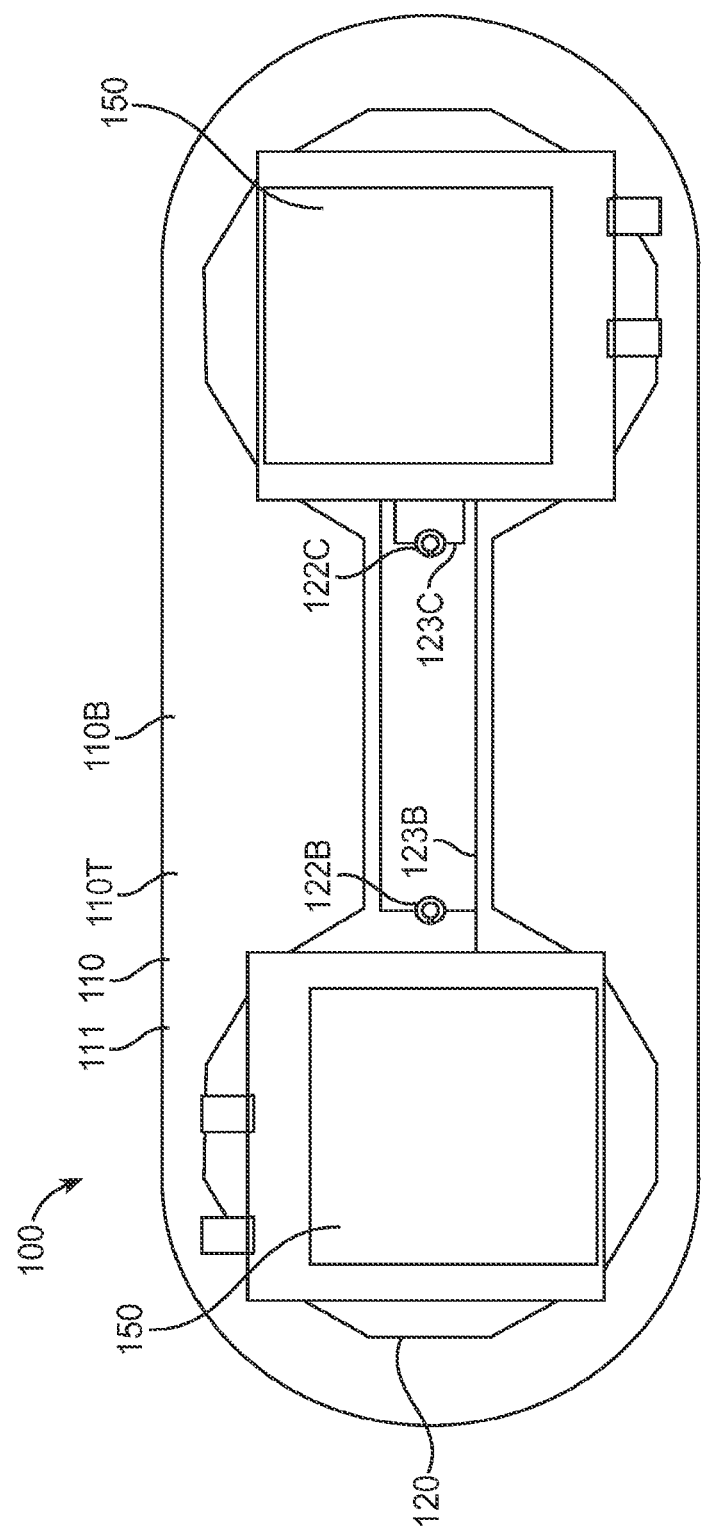
FIG. 1E shows batteries positioned over the printed circuit board and electronic components as in FIG. 1D.

Embodiments of the present invention relate to patient monitoring. Although embodiments make specific reference to monitoring impedance and electrocardiogram signals with an adherent patch, the system methods and device described herein may be applicable to any application in which physiological monitoring is used, for example wireless physiological monitoring for extended periods.

Decompensation is failure of the heart to maintain adequate blood circulation. Although the heart can maintain at least some pumping of blood, the quantity is inadequate to maintain healthy tissues. Several symptoms can result from decompensation including pulmonary congestion, breathlessness, faintness, cardiac palpitation, edema of the extremities, and enlargement of the liver. Cardiac decompensation can result in slow or sudden death. Sudden Cardiac Arrest (hereinafter "SCA"), also referred to as sudden cardiac death, is an abrupt loss of cardiac pumping function that can be caused by a ventricular arrhythmia, for example ventricular tachycardia and/or ventricular fibrillation. Although decompensation and SCA can be related in that patients with decompensation are also at an increased risk for SCA, decompensation is primarily a mechanical dysfunction caused by inadequate blood flow, and SCA is primarily an electrical dysfunction caused by inadequate and/or inappropriate electrical signals of the heart.

In many embodiments, the adherent devices described herein may be used for 90 day monitoring, or more, and may comprise completely disposable components and/or reusable components, and can provide reliable data acquisition and transfer. In many embodiments, the patch is configured for patient comfort, such that the adherent patch can be worn and/or tolerated by the patient for extended periods, for example 90 days or more. The patch may be worn continuously for at least seven days, for example 14 days, and then replaced with another patch. Adherent devices with comfortable patches that can be worn for extended periods and in which patches can be replaced and the electronics modules reused are described in U.S. Pat. App. Nos. 60/972,537, entitled "Adherent Device with Multiple Physiological Sensors"; and 60/972,629, entitled "Adherent Device with Multiple Physiological Sensors", both filed on Sep. 14, 2007, the full disclosures of which have been previously incorporated herein by reference. In many embodiments, the adherent patch comprises a tape, which comprises a material, preferably breathable, with an adhesive, such that trauma to the patient skin can be minimized while the patch is worn for the extended period. The printed circuit board may comprise a flex printed circuit board that can flex with the patient to provide improved patient comfort.

FIG. 1A shows a patient P and a monitoring system 10. Patient P comprises a midline M, a first side 51, for example a right side, and a second side S2, for example a left side. Monitoring system 10 comprises an adherent device 100. Adherent device 100 can be adhered to a patient P at many locations, for example thorax T of patient P. In many embodiments, the adherent device may adhere to one side of the patient, from which side data can be collected. Work in relation with embodiments of the present invention suggests that location on a side of the patient can provide comfort for the patient while the device is adhered to the patient.

Monitoring system 10 includes components to transmit data to a remote center 106. Remote center 106 can be located in a different building from the patient, for example in the same town as the patient, and can be located as far from the patient as a separate continent from the patient, for example the patient located on a first continent and the remote center located on a second continent. Adherent device 100 can communicate wirelessly to an intermediate device 102, for example with a single wireless hop from the adherent device on the patient to the intermediate device. Intermediate device 102 can communicate with remote center 106 in many ways, for example with an internet connection and/or with a cellular connection. In many embodiments, monitoring system 10 comprises a distributed processing system with at least one processor comprising a tangible medium of device 100, at least one processor 102P of intermediate device 102, and at least one processor 106P at remote center 106, each of which processors can be in electronic communication with the other processors. At least one processor 102P comprises a tangible medium 102T, and at least one processor 106P comprises a tangible medium 106T. Remote processor 106P may comprise a backend server located at the remote center. Remote center 106 can be in communication with a health care provider 108A with a communication system 107A, such as the Internet, an intranet, phone lines, wireless and/or satellite phone. Health care provider 108A, for example a family member, can be in communication with patient P with a communication, for example with a two way communication system, as indicated by arrow 109A, for example by cell phone, email, landline. Remote center 106 can be in communication with a health care professional, for example a physician 108B, with a communication system 107B, such as the Internet, an intranet, phone lines, wireless and/or satellite phone. Physician 108B can be in communication with patient P with a communication, for example with a two way communication system, as indicated by arrow 109B, for example by cell phone, email, landline. Remote center 106 can be in communication with an emergency responder 108C, for example a 911 operator and/or paramedic, with a communication system 107C, such as the Internet, an intranet, phone lines, wireless and/or satellite phone. Emergency responder 108C can travel to the patient as indicated by arrow 109C. Thus, in many embodiments, monitoring system 10 comprises a closed loop system in which patient care can be monitored and implemented from the remote center in response to signals from the adherent device.

In many embodiments, the adherent device may continuously monitor physiological parameters, communicate wirelessly with a remote center, and provide alerts when necessary. The system may comprise an adherent patch, which attaches to the patient's thorax and contains sensing electrodes, battery, memory, logic, and wireless communication capabilities. In some embodiments, the patch can communicate with the remote center, via the intermediate device in the patient's home. In some embodiments, remote center 106 receives the patient data and applies a patient evaluation algorithm, for example the prediction algorithm to predict cardiac decompensation. In some embodiments, the algorithm may comprise an algorithm to predict impending cardiac decompensation is described in U.S. Pat. App. No. 60/972,512, the full disclosure of which has been previously incorporated herein by reference. When a flag is raised, the center may communicate with the patient, hospital, nurse, and/or physician to allow for therapeutic intervention, for example to prevent decompensation.

The adherent device may be affixed and/or adhered to the body in many ways. For example, with at least one of the following an adhesive tape, a constant-force spring, suspenders around shoulders, a screw-in microneedle electrode, a pre-shaped electronics module to shape fabric to a thorax, a pinch onto roll of skin, or transcutaneous anchoring. Patch and/or device replacement may occur with a keyed patch (e.g. two-part patch), an outline or anatomical mark, a low-adhesive guide (place guide|remove old patch|place new patch|remove guide), or a keyed attachment for chatter reduction. The patch and/or device may comprise an adhesiveless embodiment (e.g. chest strap), and/or a low-irritation adhesive for sensitive skin. The adherent patch and/or device can comprise many shapes, for example at least one of a dogbone, an hourglass, an oblong, a circular or an oval shape.

In many embodiments, the adherent device may comprise a reusable electronics module with replaceable patches, and each of the replaceable patches may include a battery. The module may collect cumulative data for approximately 90 days and/or the entire adherent component (electronics+patch) may be disposable. In a completely disposable embodiment, a "baton" mechanism may be used for data transfer and retention, for example baton transfer may include baseline information. In some embodiments, the device may have a rechargeable module, and may use dual battery and/or electronics modules, wherein one module 101A can be recharged using a charging station 103 while the other module 101B is placed on the adherent patch with connectors. In some embodiments, the intermediate device 102 may comprise the charging module, data transfer, storage and/or transmission, such that one of the electronics modules can be placed in the intermediate device for charging and/or data transfer while the other electronics module is worn by the patient.

System 10 can perform the following functions: initiation, programming, measuring, storing, analyzing, communicating, predicting, and displaying. The adherent device may contain a subset of the following physiological sensors: bioimpedance, respiration, respiration rate variability, heart rate (ave, min, max), heart rhythm, hear rate variability (HRV), heart rate turbulence (HRT), heart sounds (e.g. S3), respiratory sounds, blood pressure, activity, wake/sleep, posture, orthopnea, temperature/heat flux, and weight. The activity sensor may comprise one or more of the following: ball switch, accelerometer, minute ventilation, HR, bioimpedance noise, skin temperature/heat flux, BP, muscle noise, posture.

The adherent device can wirelessly communicate with remote center 106. The communication may occur directly (via a cellular or Wi-Fi network), or indirectly through intermediate device 102. Intermediate device 102 may consist of multiple devices, which can communicate wired or wirelessly to relay data to remote center 106.

In many embodiments, instructions are transmitted from remote site 106 to a processor supported with the adherent patch on the patient, and the processor supported with the patient can receive updated instructions for the patient treatment and/or monitoring, for example while worn by the patient.

FIG. 1B shows a bottom view of adherent device 100 as in FIG. 1A comprising an adherent patch 110. Adherent patch 110 comprises a first side, or a lower side 110A, that is oriented toward the skin of the patient when placed on the patient. In many embodiments, adherent patch 110 comprises a tape 110T which is a material, preferably breathable, with an adhesive 116A. Patient side 110A comprises adhesive 116A to adhere the patch 110 and adherent device 100 to patient P. Electrodes 112A, 112B, 112C and 112D are affixed to adherent patch 110. In many embodiments, at least four electrodes are attached to the patch, for example six electrodes. In some embodiments the patch comprises two electrodes, for example two electrodes to measure the electrocardiogram (ECG) of the patient. Gel 114A, gel 114B, gel 114C and gel 114D can each be positioned over electrodes 112A, 112B, 112C and 112D, respectively, to provide electrical conductivity between the electrodes and the skin of the patient. In many embodiments, the electrodes can be affixed to the patch 110, for example with known methods and structures such as rivets, adhesive, stitches, etc. In many embodiments, patch 110 comprises a breathable material to permit air and/or vapor to flow to and from the surface of the skin.

FIG. 1C shows a top view of the adherent patch 100, as in FIG. 1B. Adherent patch 100 comprises a second side, or upper side 110B. In many embodiments, electrodes 112A, 112B, 112C and 112D extend from lower side 110A through adherent patch 110 to upper side 110B. An adhesive 116B can be applied to upper side 110B to adhere structures, for example a breathable cover, to the patch such that the patch can support the electronics and other structures when the patch is adhered to the patient. The PCB may comprise completely flex PCB, rigid PCB, rigid PCB combined flex PCB and/or rigid PCB boards connected by cable.

FIG. 1D shows a printed circuit boards and electronic components over adherent patch 110, as in FIG. 1A to 1C. In some embodiments, a printed circuit board (PCB), for example flex printed circuit board 120, may be connected to electrodes 112A, 112B, 112C and 112D with connectors 122A, 122B, 122C and 122D. Flex printed circuit board 120 can include traces 123A, 123B, 123C and 123D that extend to connectors 122A, 122B, 122C and 122D, respectively, on the flex PCB. Connectors 122A, 122B, 122C and 122D can be positioned on flex printed circuit board 120 in alignment with electrodes 112A, 112B, 112C and 112D so as to electrically couple the flex PCB with the electrodes. In some embodiments, connectors 122A, 122B, 122C and 122D may comprise insulated wires and/or a film with conductive ink that provide strain relief between the PCB and the electrodes. For example, connectors 122A, 122B, 122C and 122D may comprise a flexible polyester film coated with conductive silver ink. In some embodiments, additional PCB's, for example rigid PCB's 120A, 120B, 120C and 120D, can be connected to flex printed circuit board 120. Electronic components 130 can be connected to flex printed circuit board 120 and/or mounted thereon. In some embodiments, electronic components 130 can be mounted on the additional PCB's.

Electronic components 130 comprise components to take physiologic measurements, transmit data to remote center 106 and receive commands from remote center 106. In many embodiments, electronics components 130 may comprise known low power circuitry, for example complementary metal oxide semiconductor (CMOS) circuitry components. Electronics components 130 comprise an activity sensor and activity circuitry 134, impedance circuitry 136 and electrocardiogram circuitry, for example ECG circuitry 136. In some embodiments, electronics circuitry 130 may comprise a microphone and microphone circuitry 142 to detect an audio signal from within the patient, and the audio signal may comprise a heart sound and/or a respiratory sound, for example an S3 heart sound and a respiratory sound with rales and/or crackles.

Electronics circuitry 130 may comprise a temperature sensor, for example a thermistor in contact with the skin of the patient, and temperature sensor circuitry 144 to measure a temperature of the patient, for example a temperature of the skin of the patient. A temperature sensor may be used to determine the sleep and wake state of the patient. The temperature of the patient can decrease as the patient goes to sleep and increase when the patient wakes up.

Work in relation to embodiments of the present invention suggests that skin temperature may effect impedance and/or hydration measurements, and that skin temperature measurements may be used to correct impedance and/or hydration measurements. In some embodiments, increase in skin temperature or heat flux can be associated with increased vasodilation near the skin surface, such that measured impedance measurement decreased, even through the hydration of the patient in deeper tissues under the skin remains substantially unchanged. Thus, use of the temperature sensor can allow for correction of the hydration signals to more accurately assess the hydration, for example extra cellular hydration, of deeper tissues of the patient, for example deeper tissues in the thorax.

Electronics circuitry 130 may comprise a processor 146. Processor 146 comprises a tangible medium, for example read only memory (ROM), electrically erasable programmable read only memory (EEPROM) and/or random access memory (RAM). Electronic circuitry 130 may comprise real time clock and frequency generator circuitry 148. In some embodiments, processor 136 may comprise the frequency generator and real time clock. The processor can be configured to control a collection and transmission of data from the impedance circuitry electrocardiogram circuitry and the accelerometer. In many embodiments, device 100 comprise a distributed processor system, for example with multiple processors on device 100.

In many embodiments, electronics components 130 comprise wireless communications circuitry 132 to communicate with remote center 106. The wireless communication circuitry can be coupled to the impedance circuitry, the electrocardiogram circuitry and the accelerometer to transmit to a remote center with a communication protocol at least one of the hydration signal, the electrocardiogram signal or the inclination signal. In specific embodiments, wireless communication circuitry is configured to transmit the hydration signal, the electrocardiogram signal and the inclination signal to the remote center with a single wireless hop, for example from wireless communication circuitry 132 to intermediate device 102. The communication protocol comprises at least one of Bluetooth, Zigbee, WiFi, WiMax, IR, amplitude modulation or frequency modulation. In many embodiments, the communications protocol comprises a two way protocol such that the remote center is capable of issuing commands to control data collection.

Intermediate device 102 may comprise a data collection system to collect and store data from the wireless transmitter. The data collection system can be configured to communicate periodically with the remote center. The data collection system can transmit data in response to commands from remote center 106 and/or in response to commands from the adherent device.

Activity sensor and activity circuitry 134 can comprise many known activity sensors and circuitry. In many embodiments, the accelerometer comprises at least one of a piezoelectric accelerometer, capacitive accelerometer or electromechanical accelerometer. The accelerometer may comprises a 3-axis accelerometer to measure at least one of an inclination, a position, an orientation or acceleration of the patient in three dimensions. Work in relation to embodiments of the present invention suggests that three dimensional orientation of the patient and associated positions, for example sitting, standing, lying down, can be very useful when combined with data from other sensors, for example ECG data and/or hydration data.

Impedance circuitry 136 can generate both hydration data and respiration data. In many embodiments, impedance circuitry 136 is electrically connected to electrodes 112A, 112B, 112C and 112D in a four pole configuration, such that electrodes 112A and 112D comprise outer electrodes that are driven with a current and comprise force electrodes that force the current through the tissue. The current delivered between electrodes 112A and 112D generates a measurable voltage between electrodes 112B and 112C, such that electrodes 112B and 112C comprise inner, sense, electrodes that sense and/or measure the voltage in response to the current from the force electrodes. In some embodiments, electrodes 112B and 112C may comprise force electrodes and electrodes 112A and 112B may comprise sense electrodes. The voltage measured by the sense electrodes can be used to measure the impedance of the patient and determine the respiration rate and/or hydration of the patient.

FIG. 1D1 shows an equivalent circuit 152 that can be used to determine optimal frequencies for measuring patient hydration. Work in relation to embodiments of the present invention indicates that the frequency of the current and/or voltage at the force electrodes can be selected so as to provide impedance signals related to the extracellular and/or intracellular hydration of the patient tissue. Equivalent circuit 152 comprises an intracellular resistance 156, or R(ICW) in series with a capacitor 154, and an extracellular resistance 158, or R(ECW). Extracellular resistance 158 is in parallel with intracellular resistance 156 and capacitor 154 related to capacitance of cell membranes. In many embodiments, impedances can be measured and provide useful information over a wide range of frequencies, for example from about 0.5 kHz to about 200 KHz. Work in relation to embodiments of the present invention suggests that extracellular resistance 158 can be significantly related extracellular fluid and to cardiac decompensation, and that extracellular resistance 158 and extracellular fluid can be effectively measured with frequencies in a range from about 0.5 kHz to about 20 kHz, for example from about 1 kHz to about 10 kHz. In some embodiments, a single frequency can be used to determine the extracellular resistance and/or fluid. As sample frequencies increase from about 10 kHz to about 20 kHz, capacitance related to cell membranes decrease the impedance, such that the intracellular fluid contributes to the impedance and/or hydration measurements. Thus, many embodiments of the present invention measure hydration with frequencies from about 0.5 kHz to about 20 kHz to determine patient hydration.

In many embodiments, impedance circuitry 136 can be configured to determine respiration of the patient. In specific embodiments, the impedance circuitry can measure the hydration at 25 Hz intervals, for example at 25 Hz intervals using impedance measurements with a frequency from about 0.5 kHz to about 20 kHz.

ECG circuitry 138 can generate electrocardiogram signals and data from two or more of electrodes 112A, 112B, 112C and 112D in many ways. In some embodiments, ECG circuitry 138 is connected to inner electrodes 112B and 122C, which may comprise sense electrodes of the impedance circuitry as described above. In some embodiments, ECG circuitry 138 can be connected to electrodes 112A and 112D so as to increase spacing of the electrodes. The inner electrodes may be positioned near the outer electrodes to increase the voltage of the ECG signal measured by ECG circuitry 138. In many embodiments, the ECG circuitry may measure the ECG signal from electrodes 112A and 112D when current is not passed through electrodes 112A and 112D, for example with switches as described in U.S. App. No. 60/972,527, the full disclosure of which has been previously incorporated herein by reference.

FIG. 1E shows batteries 150 positioned over the flex printed circuit board and electronic components as in FIG. 1D. Batteries 150 may comprise rechargeable batteries that can be removed and/or recharged. In some embodiments, batteries 150 can be removed from the adherent patch and recharged and/or replaced.

Figure 1F:
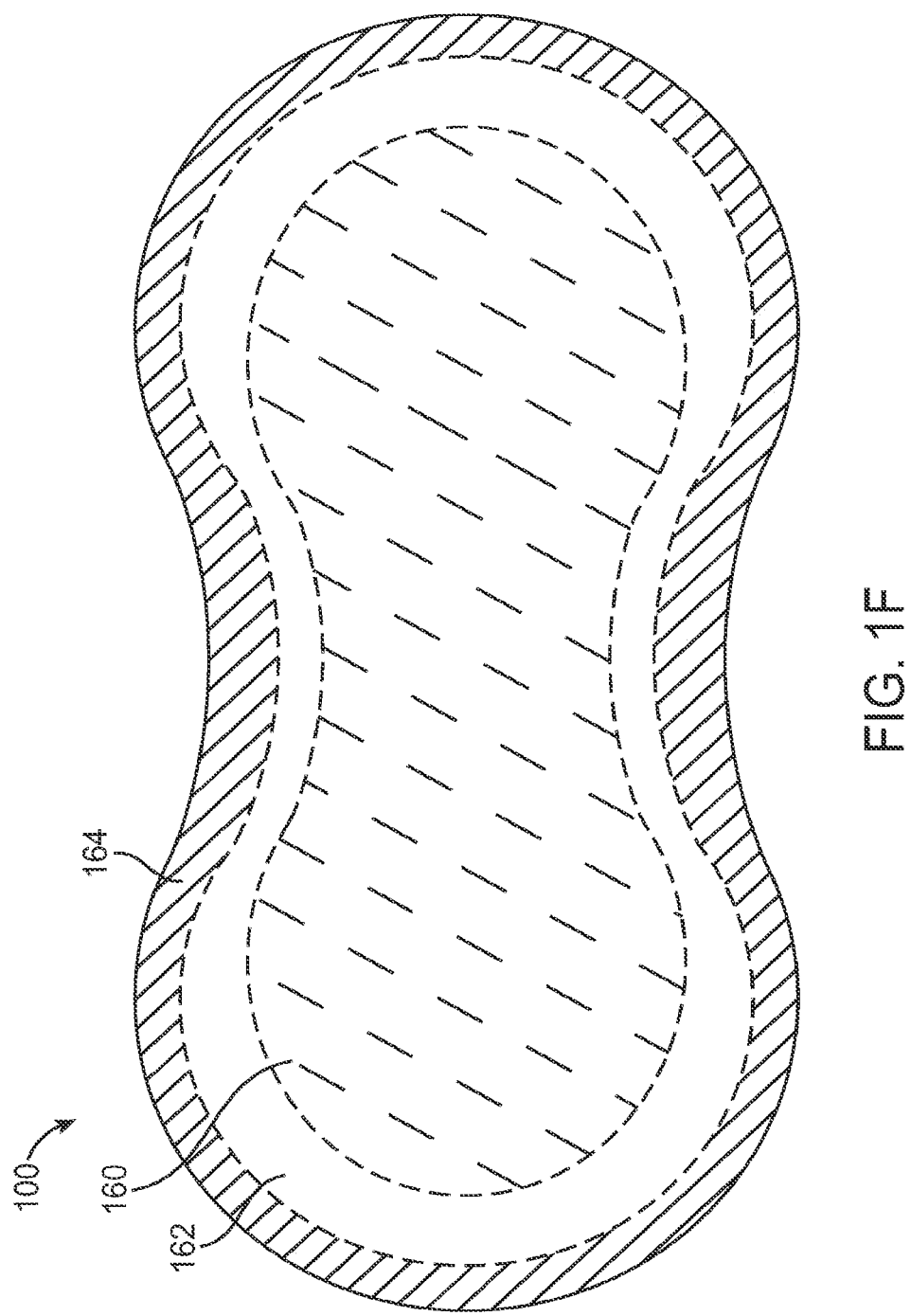
FIG. 1F shows a top view of an electronics housing and a breathable cover over the batteries, electronic components and printed circuit board as in FIG. 1E.

FIG. 1F shows a top view of a cover 162 over the batteries, electronic components and flex printed circuit board as in FIGS. 1A to 1E. In many embodiments, an electronics housing 160 may be disposed under cover 162 to protect the electronic components, and in some embodiments electronics housing 160 may comprise an encapsulant over the electronic components and PCB. In some embodiments, cover 162 can be adhered to adherent patch 110 with an adhesive 164 on an underside of cover 162. In many embodiments, electronics housing 160 may comprise a water proof material, for example a sealant adhesive such as epoxy or silicone coated over the electronics components and/or PCB. In some embodiments, electronics housing 160 may comprise metal and/or plastic. Metal or plastic may be potted with a material such as epoxy or silicone.

Cover 162 may comprise many known biocompatible cover, casing and/or housing materials, such as elastomers, for example silicone. The elastomer may be fenestrated to improve breathability. In some embodiments, cover 162 may comprise many known breathable materials, for example polyester, polyamide, and/or elastane (Spandex™). The breathable fabric may be coated to make it water resistant, waterproof, and/or to aid in wicking moisture away from the patch.

Figure 1H:
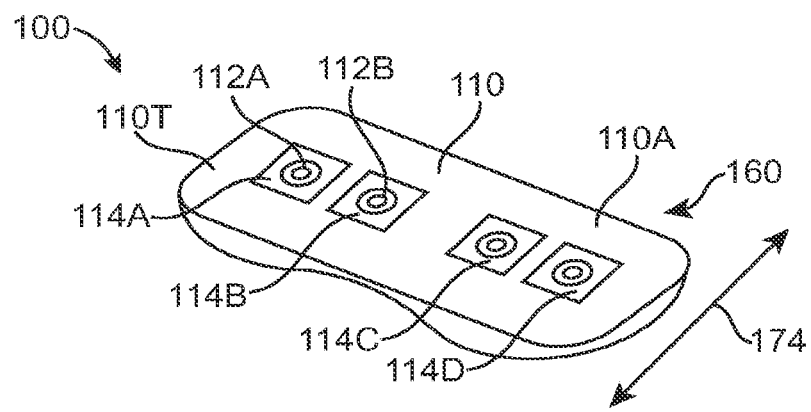
FIG. 1H shown a bottom isometric view of the adherent device as in FIGS. 1A to 1G.
Figure 1G:
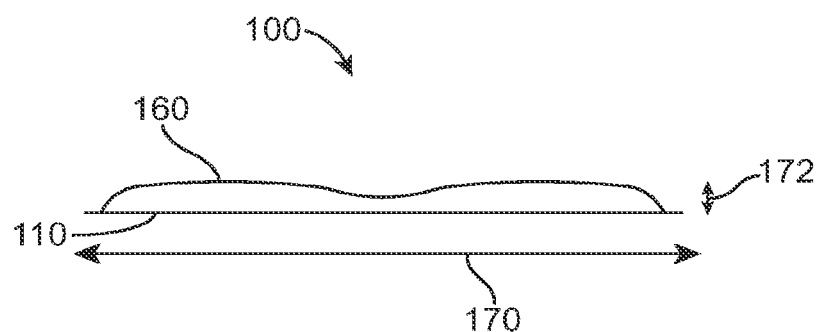
FIG. 1G shows a side view of the adherent device as in FIGS. 1A to 1F.

FIG. 1G shows a side view of adherent device 100 as in FIGS. 1A to 1F. Adherent device 100 comprises a maximum dimension, for example a length 170 from about 4 to 10 inches (from about 100 mm to about 250 mm), for example from about 6 to 8 inches (from about 150 mm to about 200 mm) In some embodiments, length 170 may be no more than about 6 inches (no more than about 150 mm) Adherent device 100 comprises a thickness 172. Thickness 172 may comprise a maximum thickness along a profile of the device. Thickness 172 can be from about 0.2 inches to about 0.4 inches (from about 5 mm to about 10 mm), for example about 0.3 inches (about 7.5 mm).

FIG. 1H shown a bottom isometric view of adherent device 100 as in FIGS. 1A to 1G. Adherent device 100 comprises a width 174, for example a maximum width along a width profile of adherent device 100. Width 174 can be from about 2 to about 4 inches (from about 50 mm to 100 mm), for example about 3 inches (about 75 mm).

Figure 1J:
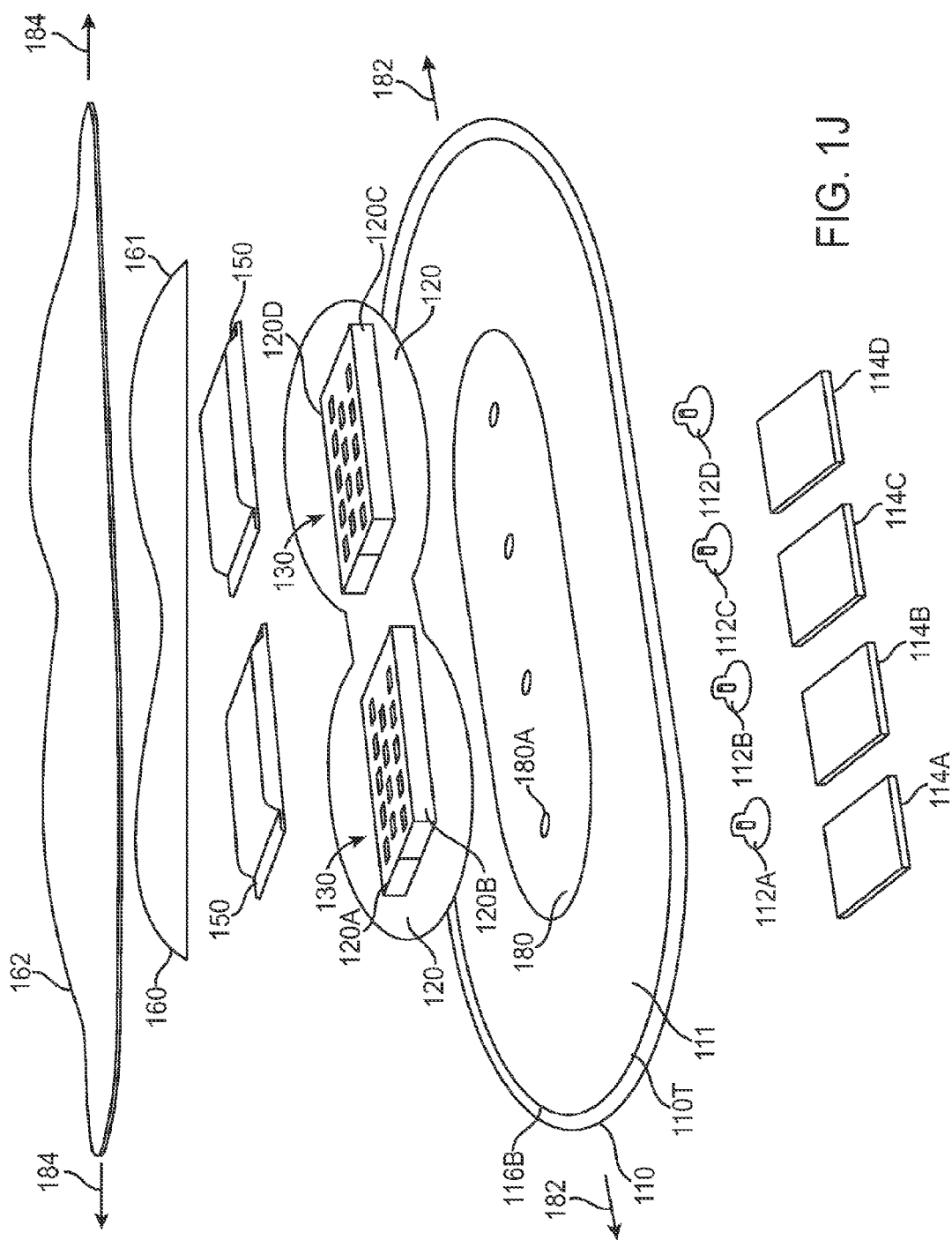

FIGS. 1I and 1J show a side cross-sectional view and an exploded view, respectively, of adherent device 100 as in FIGS. 1A to 1H. Device 100 comprises several layers. Gel 114A, or gel layer, is positioned on electrode 112A to provide electrical conductivity between the electrode and the skin. Electrode 112A may comprise an electrode layer. Adherent patch 110 may comprise a layer of breathable tape 110T, for example a known breathable tape, such as tricot-knit polyester fabric. An adhesive 116A, for example a layer of acrylate pressure sensitive adhesive, can be disposed on underside 110A of adherent patch 110.

A gel cover 180, or gel cover layer, for example a polyurethane non-woven tape, can be positioned over patch 110 comprising the breathable tape. A PCB layer, for example flex printed circuit board 120, or flex PCB layer, can be positioned over gel cover 180 with electronic components 130 connected and/or mounted to flex printed circuit board 120, for example mounted on flex PCB so as to comprise an electronics layer disposed on the flex PCB layer. In many embodiments, the adherent device may comprise a segmented inner component, for example the PCB may be segmented to provide at least some flexibility. In many embodiments, the electronics layer may be encapsulated in electronics housing 160 which may comprise a waterproof material, for example silicone or epoxy. In many embodiments, the electrodes are connected to the PCB with a flex connection, for example trace 123A of flex printed circuit board 120, so as to provide strain relive between the electrodes 112A, 112B, 112C and 112D and the PCB.

Gel cover 180 can inhibit flow of gel 114A and liquid. In many embodiments, gel cover 180 can inhibit gel 114A from seeping through breathable tape 110T to maintain gel integrity over time. Gel cover 180 can also keep external moisture, for example liquid water, from penetrating though the gel cover into gel 114A while allowing moisture vapor from the gel, for example moisture vapor from the skin, to transmit through the gel cover.

In many embodiments, cover 162 can encase the flex PCB and/or electronics and can be adhered to at least one of the electronics, the flex PCB or adherent patch 110, so as to protect at least the electronics components and the PCB. Cover 162 can attach to adherent patch 110 with adhesive 116B. Cover 162 can comprise many known biocompatible cover materials, for example silicone. Cover 162 can comprise an outer polymer cover to provide smooth contour without limiting flexibility. In many embodiments, cover 162 may comprise a breathable fabric. Cover 162 may comprise many known breathable fabrics, for example breathable fabrics as described above. In some embodiments, the breathable cover may comprise a breathable water resistant cover. In some embodiments, the breathable fabric may comprise polyester, nylon, polyamide, and/or elastane (Spandex™) to allow the breathable fabric to stretch with body movement. In some embodiments, the breathable tape may contain and elute a pharmaceutical agent, such as an antibiotic, anti-inflammatory or antifungal agent, when the adherent device is placed on the patient.

The breathable cover 162 and adherent patch 110 comprise breathable tape can be configured to couple continuously for at least one week the at least one electrode to the skin so as to measure breathing of the patient. The breathable tape may comprise the stretchable breathable material with the adhesive and the breathable cover may comprises a stretchable water resistant material connected to the breathable tape, as described above, such that both the adherent patch and cover can stretch with the skin of the patient. Arrows 182 show stretching of adherent patch 110, and the stretching of adherent patch can be at least two dimensional along the surface of the skin of the patient. As noted above, connectors 122A, 122B, 122C and 122D between PCB 130 and electrodes 112A, 112B, 112C and 112D may comprise insulated wires that provide strain relief between the PCB and the electrodes, such that the electrodes can move with the adherent patch as the adherent patch comprising breathable tape stretches. Arrows 184 show stretching of cover 162, and the stretching of the cover can be at least two dimensional along the surface of the skin of the patient. Cover 162 can be attached to adherent patch 110 with adhesive 116B such that cover 162 stretches and/or retracts when adherent patch 110 stretches and/or retracts with the skin of the patient. For example, cover 162 and adherent patch 110 can stretch in two dimensions along length 170 and width 174 with the skin of the patient, and stretching along length 170 can increase spacing between electrodes. Stretching of the cover and adherent patch 110, for example in two dimensions, can extend the time the patch is adhered to the skin as the patch can move with the skin such that the patch remains adhered to the skin. Electronics housing 160 can be smooth and allow breathable cover 162 to slide over electronics housing 160, such that motion and/or stretching of cover 162 is slidably coupled with housing 160. The printed circuit board can be slidably coupled with adherent patch 110 that comprises breathable tape 110T, such that the breathable tape can stretch with the skin of the patient when the breathable tape is adhered to the skin of the patient, for example along two dimensions comprising length 170 and width 174. Electronics components 130 can be affixed to printed circuit board 120, for example with solder, and the electronics housing can be affixed over the PCB and electronics components, for example with dip coating, such that electronics components 130, printed circuit board 120 and electronics housing 160 are coupled together. Electronics components 130, printed circuit board 120, and electronics housing 160 are disposed between the stretchable breathable material of adherent patch 110 and the stretchable water resistant material of cover 160 so as to allow the adherent patch 110 and cover 160 to stretch together while electronics components 130, printed circuit board 120, and electronics housing 160 do not stretch substantially, if at all. This decoupling of electronics housing 160, printed circuit board 120 and electronic components 130 can allow the adherent patch 110 comprising breathable tape to move with the skin of the patient, such that the adherent patch can remain adhered to the skin for an extended time of at least one week, for example two or more weeks.

An air gap 169 may extend from adherent patch 110 to the electronics module and/or PCB, so as to provide patient comfort. Air gap 169 allows adherent patch 110 and breathable tape 110T to remain supple and move, for example bend, with the skin of the patient with minimal flexing and/or bending of printed circuit board 120 and electronic components 130, as indicated by arrows 186. Printed circuit board 120 and electronics components 130 that are separated from the breathable tape 110T with air gap 169 can allow the skin to release moisture as water vapor through the breathable tape, gel cover, and breathable cover. This release of moisture from the skin through the air gap can minimize, and even avoid, excess moisture, for example when the patient sweats and/or showers.

The breathable tape of adherent patch 110 may comprise a first mesh with a first porosity and gel cover 180 may comprise a breathable tape with a second porosity, in which the second porosity is less than the first porosity to minimize, and even inhibit, flow of the gel through the breathable tape. The gel cover may comprise a polyurethane film with the second porosity.

In many embodiments, the adherent device comprises a patch component and at least one electronics module. The patch component may comprise adherent patch 110 comprising the breathable tape with adhesive coating 116A, at least one electrode, for example electrode 114A and gel 114. The at least one electronics module can be separable from the patch component. In many embodiments, the at least one electronics module comprises the flex printed circuit board 120, electronic components 130, electronics housing 160 and cover 162, such that the flex printed circuit board, electronic components, electronics housing and cover are reusable and/or removable for recharging and data transfer, for example as described above. In many embodiments, adhesive 116B is coated on upper side 110A of adherent patch 110B, such that the electronics module can be adhered to and/or separated from the adhesive component. In specific embodiments, the electronic module can be adhered to the patch component with a releasable connection, for example with Velcro™, a known hook and loop connection, and/or snap directly to the electrodes. Two electronics modules can be provided, such that one electronics module can be worn by the patient while the other is charged, as described above. Monitoring with multiple adherent patches for an extended period is described in U.S. Pat. App. No. 60/972,537, the full disclosure of which has been previously incorporated herein by reference. Many patch components can be provided for monitoring over the extended period. For example, about 12 patches can be used to monitor the patient for at least 90 days with at least one electronics module, for example with two reusable electronics modules.

At least one electrode 112A can extend through at least one aperture 180A in the breathable tape 110 and gel cover 180.

In some embodiments, the adhesive patch may comprise a medicated patch that releases a medicament, such as antibiotic, beta-blocker, ACE inhibitor, diuretic, or steroid to reduce skin irritation. The adhesive patch may comprise a thin, flexible, breathable patch with a polymer grid for stiffening. This grid may be anisotropic, may use electronic components to act as a stiffener, may use electronics-enhanced adhesive elution, and may use an alternating elution of adhesive and steroid.

FIG. 1K shows at least one electrode 190 configured to electrically couple to a skin of the patient through a breathable tape 192. In many embodiments, at least one electrode 190 and breathable tape 192 comprise electrodes and materials similar to those described above. Electrode 190 and breathable tape 192 can be incorporated into adherent devices as described above, so as to provide electrical coupling between the skin an electrode through the breathable tape, for example with the gel.

Figure 2A:
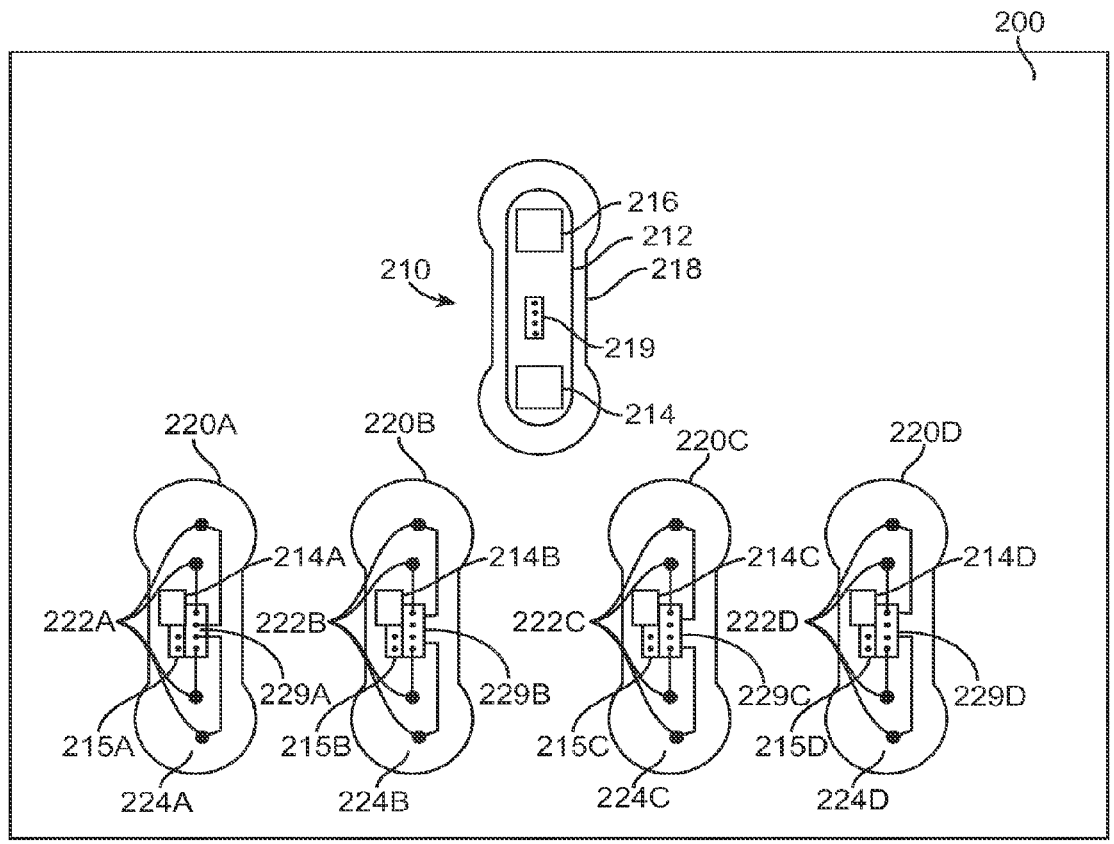
FIGS. 2A to 2C show a system to monitor a patient for an extended period comprising a reusable electronic component and a plurality of disposable patch components, according to embodiments of the present invention.
Figure 2B:
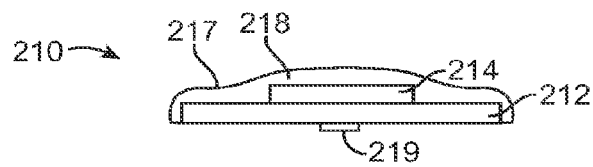
Figure 2C:
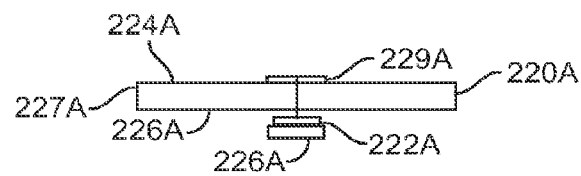

FIGS. 2A to 2C show a schematic illustration of a system 200 to monitor a patient for an extended period. FIG. 2A shows a schematic illustration of system 200 comprising a reusable electronics module 210 and a plurality of disposable patch components comprising a first disposable patch component 220A, a second disposable patch component 220B, a third disposable patch component 220C and a fourth disposable patch component 220D. Although four patch components a shown the plurality may comprise as few as two patch component and as many as three or more patch components, for example 25 patch components.

FIG. 2B shows a schematic illustration of a side cross-sectional view of reusable electronics module 210. Reusable electronics module 210 may comprises many of the structures described above that may comprise the electronics module. In many embodiments, reusable electronics module 210 comprises a PCB, for example a flex PCB 212, electronics components 216, batteries 216, and a cover 217, for example as described above. In some embodiments, reusable electronics module 210 may comprise an electronics housing over the electronics components and/or PCB as described above. The electronics components may comprise circuitry and/or sensors for measuring ECG signals, hydration impedance signals, respiration impedance signals and accelerometer signals, for example as described above. In many embodiments, reusable electronics module 210 comprises a connector 219 adapted to connect to each of the disposable patch components, sequentially, for example one disposable patch component at a time. Connector 219 can be formed in many ways, and may comprise known connectors as described above, for example a snap. In some embodiments, the connectors on the electronics module and adhesive component can be disposed at several locations on the reusable electronics module and disposable patch component, for example near each electrode, such that each electrode can couple directly to a corresponding location on the flex PCB of the reusable electronics component.

Alternatively or in combination with batteries 216, each of the plurality of disposable patch components may comprise a disposable battery. For example first disposable patch component 220A may comprise a disposable battery 214A; second disposable patch component 220B may comprise a disposable battery 214B; third disposable patch component 220C may comprise a disposable battery 214C; and a fourth disposable patch component 220D may comprise a disposable battery 214D. Each of the disposable batteries, 214A, 214B, 214C and 214D may be affixed to each of disposable patches 220A, 220B, 220C and 220D, respectively, such that the batteries are adhered to the disposable patch component before, during and after the respective patch component is adhered to the patient. Each of the disposable batteries, 214A, 214B, 214C and 214D may be coupled to connectors 215A, 215B, 215C and 215D, respectively. Each of connectors 215A, 215B, 215C and 215D can be configured to couple to a connector of the reusable module 220, so as to power the reusable module with the disposable battery coupled thereto. Each of the disposable batteries, 214A, 214B, 214C and 214D may be coupled to connectors 215A, 215B, 215C and 215D, respectively, such that the batteries are not coupled to the electrodes of the respective patch component, so as to minimize, and even avoid, degradation of the electrodes and/or gel during storage when each disposable battery is adhered to each respective disposable patch component.

FIG. 2C shows a schematic illustration first disposable patch component 220A of the plurality of disposable patch components that is similar to the other disposable patch components, for example second disposable patch component 220B, third disposable patch component 220C and fourth disposable patch component 220C. The disposable patch component comprises a breathable tape 227A, an adhesive 226A on an underside of breathable tape 227A to adhere to the skin of the patient, and at least four electrodes 222A. The at least four electrodes 224A are configured to couple to the skin of a patient, for example with a gel 226A, in some embodiments the electrodes may extend through the breathable tape to couple directly to the skin of the patient with aid form the gel. In some embodiments, the at least four electrodes may be indirectly coupled to the skin through a gel and/or the breathable tape, for example as described above. A connector 229A on the upper side of the disposable adhesive component can be configured for attachment to connector 219 on reusable electronics module 210 so as to electrically couple the electrodes with the electronics module. The upper side of the disposable patch component may comprise an adhesive 224A to connect the disposable patch component to the reusable electronics module. The reusable electronics module can be adhered to the patch component with many additional known ways to adhere components, for example with Velcro™ comprising hooks and loops, snaps, a snap fit, a lock and key mechanisms, magnets, detents and the like.

Figure 2D:
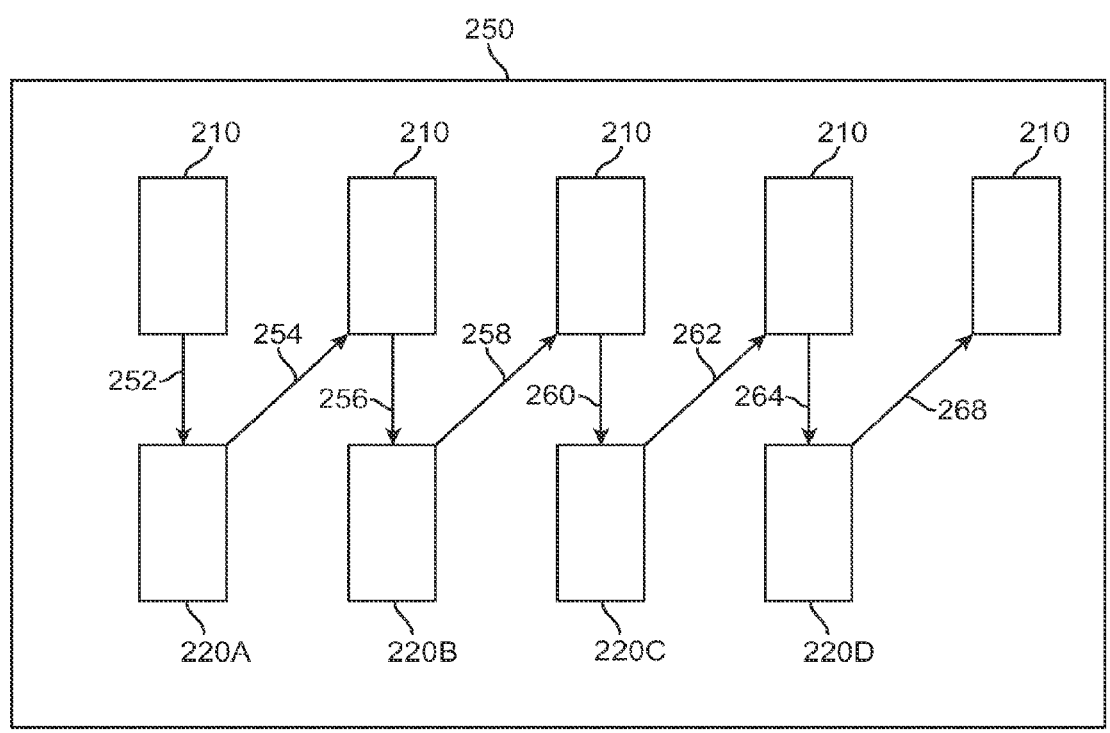
FIG. 2D shows a method of using the system as in FIGS. 2A to 2C.

FIG. 2D shows a method 250 of using system 200, as in FIGS. 2A to 2C. A step 252 adheres electronics module 210 to first disposable adherent patch component 220A of the plurality of adherent patch components and adheres the first disposable patch component to the skin of the patient, for example with the first adherent patch component adhered to the reusable electronics module. A step 254 removes the first disposable adherent patch from the patient and separates first disposable adherent patch component 220A from reusable electronics module 210. A step 256 adheres electronics module 210 to second disposable adherent patch component 220B and adheres the second disposable patch component to the skin of the patient, for example with the second adherent patch component adhered to the reusable electronics module. A step 258 removes the second disposable adherent patch from the patient and separates second disposable adherent patch component 220B from reusable electronics module 210. A step 260 adheres electronics module 210 to third disposable adherent patch component 220C and adheres the third disposable patch component to the skin of the patient, for example with the third adherent patch component adhered to the reusable electronics module. A step 262 removes the third disposable adherent patch from the patient and separates third disposable adherent patch component 220C from reusable electronics module 210. A step 264 adheres electronics module 210 to fourth disposable adherent patch component 220D and adheres the fourth disposable patch component to the skin of the patient, for example with the third adherent patch component adhered to the reusable electronics module. A step 268 removes the fourth disposable adherent patch from the patient and separates fourth disposable adherent patch component 220D from reusable electronics module 210.

In many embodiments, physiologic signals, for example ECG, hydration impedance, respiration impedance and accelerometer impedance are measured when the adherent patch component is adhered to the patient, for example when any of the first, second, third or fourth disposable adherent patches is adhered to the patient.

FIGS. 3A to 3D show a method 300 of monitoring a patient for an extended period with adherent patches alternatively adhered to a right side 302 and a left side 304 of the patient. Work in relation to embodiments of the present invention suggests that repeated positioning of a patch at the same location can irritate the skin and may cause patient discomfort. This can be avoided by alternating the patch placement between left and right sides of the patient, often a front left and a front right side of the patient where the patient can reach easily to replace the patch. In some embodiments, the patch location can be alternated on the same side of the patient, for example higher and/or lower on the same side of the patient without substantial overlap to allow the skin to recover and/or heal. In many embodiments, the patch can be symmetrically positioned on an opposite side such that signals may be similar to a previous position of the patch symmetrically disposed on an opposite side of the patient. In many embodiments, the duration between removal of one patch and placement of the other patch can be short, such that any differences between the signals may be assumed to be related to placement of the patch, and these differences can be removed with signal processing.

In many embodiments each patch comprises at least four electrodes configured to measure an ECG signal and impedance, for example hydration and/or respiration impedance. In many embodiments, the patient comprises a midline 306, with first side, for example right side 302, and second side, for example left side 304, symmetrically disposed about the midline. A step 310 adheres a first adherent patch 312 to at a first location 314 on a first side 302 of the patient for a first period of time, for example about 1 week. While the adherent patch 312 is position at first location 314 on the first side of the patient, the electrodes of the patch are coupled to the skin of the patient to measure the ECG signal and impedance signals.

A step 320 removes patch 312 and adheres a second adherent patch 322 at a second location 324 on a second side 206 of the patient for a second period of time, for example about 1 week. In many embodiments, second location 324 can be symmetrically disposed opposite first location 314 across midline 304, for example so as to minimize changes in the sequential impedance signals measured from the second side and first side. While adherent patch 322 is position at second location 324 on the second side of the patient, the electrodes of the patch are coupled to the skin of the patient to measure the ECG signal and impedance signals. In many embodiments, while adherent patch 322 is positioned at second location 324, skin at first location 314 can heal and recover from adherent coverage of the first patch. In many embodiments, second location 324 is symmetrically disposed opposite first location 314 across midline 304, for example so as to minimize changes in the impedance signals measured between the first side and second side. In many embodiments, the duration between removal of one patch and placement of the other patch can be short, such that any differences between the signals may be assumed to be related to placement of the patch, and these differences can be removed with signal processing.

A step 330 removes second patch 322 and adheres a third adherent patch 332 at a third location 334 on the first side, for example right side 302, of the patient for a third period of time, for example about 1 week. In many embodiments, third location 334 can be symmetrically disposed opposite second location 324 across midline 304, for example so as to minimize changes in the sequential impedance signals measured from the third side and second side. In many embodiments, third location 334 substantially overlaps with first location 314, so as to minimize differences in measurements between the first adherent patch and third adherent patch that may be due to patch location. While adherent patch 332 is positioned at third location 334 on the first side of the patient, the electrodes of the patch are coupled to the skin of the patient to measure the ECG signal and impedance signals. In many embodiments, while adherent patch 332 is positioned at third location 334, skin at second location 324 can heal and recover from adherent coverage of the second patch. In many embodiments, the duration between removal of one patch and placement of the other patch can be short, such that any differences between the signals may be assumed to be related to placement of the patch, and these differences can be removed with signal processing.

A step 340 removes third patch 332 and adheres a fourth adherent patch 342 at a fourth location 344 on the second side, for example left side 306, of the patient for a fourth period of time, for example about 1 week. In many embodiments, fourth location 344 can be symmetrically disposed opposite third location 334 across midline 304, for example so as to minimize changes in the sequential impedance signal measured from the fourth side and third side. In many embodiments, fourth location 344 substantially overlaps with second location 324, so as to minimize differences in measurements between the second adherent patch and fourth adherent patch that may be due to patch location. While adherent patch 342 is positioned at fourth location 344 on the second side of the patient, the electrodes of the patch are coupled to the skin of the patient to measure the ECG signal and impedance signals. In many embodiments, while adherent patch 342 is positioned at fourth location 324, skin at third location 334 can heal and recover from adherent coverage of the third patch. In many embodiments, the duration between removal of one patch and placement of the other patch can be short, such that any differences between the signals may be assumed to be related to placement of the patch, and these differences can be removed with signal processing.

It should be appreciated that the specific steps illustrated in FIGS. 3A to 3D provide a particular method of monitoring a patient for an extended period, according to an embodiment of the present invention. Other sequences of steps may also be performed according to alternative embodiments. For example, alternative embodiments of the present invention may perform the steps outlined above in a different order. Moreover, the individual steps illustrated in FIGS. 3A to 3D may include multiple sub-steps that may be performed in various sequences as appropriate to the individual step. Furthermore, additional steps may be added or removed depending on the particular applications. One of ordinary skill in the art would recognize many variations, modifications, and alternatives.

Figure 4A:
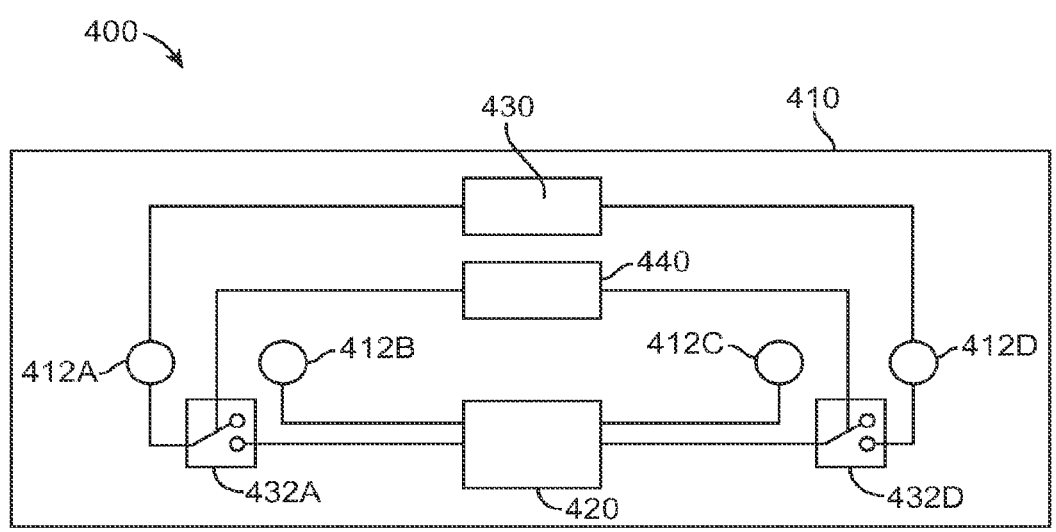
FIG. 4A shows an adherent device to measure an impedance signal and an electrocardiogram signal, according to embodiments of the present invention.

FIG. 4A shows a monitoring system 400 comprising an adherent device 410 to measure an impedance signal and an electrocardiogram signal. Device 410 may comprise wireless communication circuitry, accelerometer sensors and/or circuitry and many sensors and electronics components and structures as described above. Adherent device 410 comprises at least four electrodes. In many embodiments, the at least four electrodes comprises four electrodes, for example a first electrode 412A, a second electrode 412B, a third electrode 412C and a fourth electrode 412D. Work in relation to embodiments of the present invention suggests that embodiments in which the at least four electrodes comprises four electrodes can decrease a footprint, or size, of the device on the patient and may provide improved patient comfort. In many embodiments, first electrode 412A and fourth electrode 412D comprise outer electrodes, and second electrode 412B and third electrode 412C comprise inner electrodes, for example in embodiments where the electrodes are arranged in an elongate pattern.

Adherent device 410 comprises impedance circuitry 420 that can be used to measure hydration and respiration of the patient, and ECG circuitry 430 that is used to measure an electrocardiogram signal of the patient. Impedance circuitry 420 comprises force circuitry connected to the outer electrodes to drive a current between the electrodes. Impedance circuitry 420 comprises sense circuitry to measure a voltage between the inner electrodes resulting from the current passed between the outer force electrodes, such that the impedance of the tissue can be determined Impedance circuitry 420 may comprise known 4-pole, or quadrature, low power circuitry. ECG circuitry 430 can be connected to the outer electrodes, or force electrodes, to measure an ECG signal. Work in relation to embodiments of the present invention suggests that this use of the outer electrodes can increase the ECG signal as compared to the inner electrodes, in some embodiments, that may be due to the increased distance between the outer electrodes. ECG circuitry 430 may comprise known ECG circuitry and components, for example low power instrumentation and/or operational amplifiers.

In many embodiments, electronic switch 432A and electronic switch 432D are connected in series between impedance circuitry 420 and electrode 412A and 412D, respectively. In many embodiments, electronic switch 432A and electronic switch 432D open such that the outer electrodes can be isolated from the impedance circuitry when the ECG circuitry measures ECG signals. When electronic switch 432A and electronic switch 432D are closed, impedance circuitry 420 can force electrical current through the outer electrodes to measure impedance. In many embodiments, electronic switch 432A and electronic switch 432D can be located in the same packaging, and may comprise CMOS, precision, analog switches with low power consumption, low leakage currents, and fast switching speeds.

A processor 440 can be connected to electronic switch 423A, electronic switch 432D, impedance circuitry 420 and ECG circuitry 430 to control measurement of the ECG and impedance signals. Processor 430 comprises a tangible medium, for example read only memory (ROM), electrically erasable programmable read only memory (EEPROM) and/or random access memory (RAM). In many embodiments, processor 440 controls the measurements such that the measurements from impedance circuitry 420 and ECG circuitry 430 are time division multiplexed in response to control signals from processor 440.

Figure 4B:
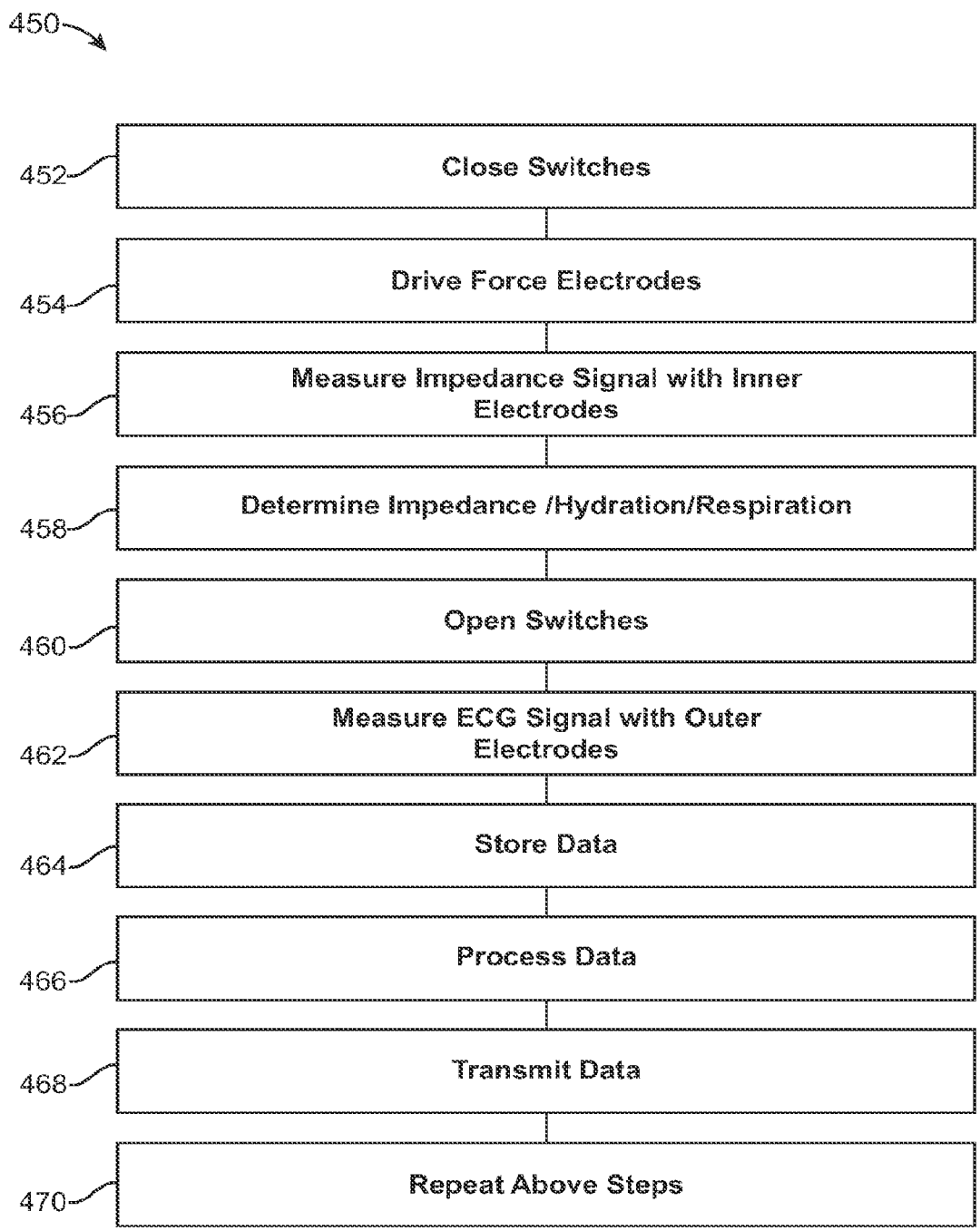
FIG. 4B shows a method of measuring the impedance signal and the electrocardiogram signal, according to embodiments of the present invention.

FIG. 4B shows a method 450 of measuring the impedance signal and the electrocardiogram signal with processor 440. A step 452 closes the switches. A step 454 drives the force electrodes. A step 456 measures the impedance signal with the inner electrodes. A step 458 determines the impedance, hydration and/or respiration from the impedance signal. A step 460 opens the switches. A step 462 measures the ECG signal with the outer electrodes. A step 464 stores the data from the impedance signals and ECG signals. A step 466 processes the data. A step 468 transmits the data, for example wirelessly to the remove center. A step 470 repeats the above steps.

It should be appreciated that the specific steps illustrated in FIG. 4B provide a particular method of measuring signals, according to an embodiment of the present invention. Other sequences of steps may also be performed according to alternative embodiments. For example, alternative embodiments of the present invention may perform the steps outlined above in a different order. Moreover, the individual steps illustrated in FIG. 4B may include multiple sub-steps that may be performed in various sequences as appropriate to the individual step. Furthermore, additional steps may be added or removed depending on the particular applications. One of ordinary skill in the art would recognize many variations, modifications, and alternatives.

Figure 5A:
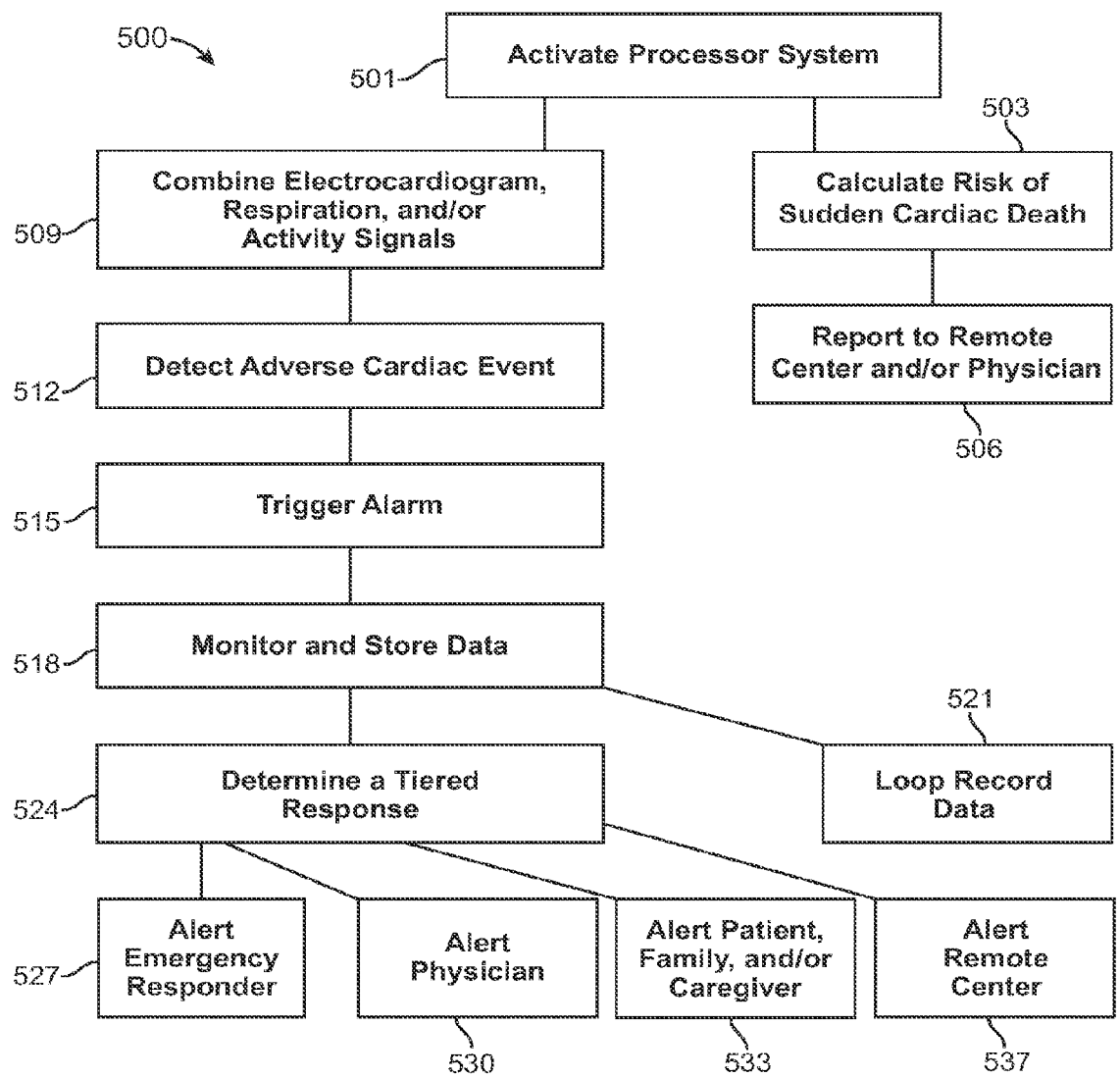
FIG. 5A shows a method for monitoring a patient and responding to a signal event.

FIG. 5A shows a method 500 for monitoring a patient and responding to a signal event. A step 501 activates a processor system. A step 503 calculates a risk of sudden cardiac death. A step 506 reports to a remote center and/or physician. A step 509 combines at least two of the electrocardiogram signal, respiration signal, and/or activity signals. A step 512 detects an adverse cardiac event. An adverse cardiac event may comprise an atrial fibrillation in response to the electrocardiogram signal and/or an acute myocardial infarction in response to an ST segment elevation of the electrocardiogram signal. A step 515 triggers an alarm. A step 518 continuously monitors and stores in tangible media at least two of the electrocardiogram signal, the respiration signal, or the activity signal. In some embodiments, a step may also comprise monitoring a high risk patent post myocardial infarction with the at least two of the electrocardiogram signal, the respiration signal or the activity signal, and/or a bradycardia of the patient at risk for sudden death. The electrocardiogram signal may comprise at least one of a Brugada Syndrome with an ST elevation and a short QT interval or long-QT interval. A step 521 loop records the aforementioned data. A step 524 determines a tiered response. In many embodiments, the tiered response may comprise tiers, or levels, appropriate to the detected status of the patient. A step 527 comprises a first tier response which alerts an emergency responder. A step 530 comprises a second tier response which alerts a physician. A step 533 comprises a third tier response which alerts a patient, family, or caregiver. A step 537 comprises a fourth tier response which alerts a remote center. A tiered response may also comprise of wirelessly transmitting the at least two of the electro cardiogram signal, the respiration signal, or the activity signal with a single wireless hop from a wireless communication circuitry to an intermediate device.

The signals can be combined in many ways. In some embodiments, the signals can be used simultaneously to determine the impending cardiac decompensation.

In some embodiments, the signals can be combined by using the at least two of the electrocardiogram signal, the respiration signal or the activity signal to look up a value in a previously existing array.

TABLE 1

Lookup Table for ECG and Respiration Signals.

| Heart Rate/Respiration | A-B bpm | C-D bpm | E-F bpm |
|---|---|---|---|
| U-V per min | N | N | Y |
| W-X per min | N | Y | Y |
| Y-Z per min | Y | Y | Y |

Table 1 shows combination of the electrocardiogram signal with the respiration signal to look up a value in a pre-existing array. For example, at a heart rate in the range from A to B bpm and a respiration rate in the range from U to V per minute triggers a response of N. In some embodiments, the values in the table may comprise a tier or level of the response, for example four tiers. In specific embodiments, the values of the look up table can be determined in response to empirical data measured for a patient population of at least about 100 patients, for example measurements on about 1000 to 10,000 patients. The look up table shown in Table 1 illustrates the use of a look up table according to one embodiment, and one will recognize that many variables can be combined with a look up table.

In some embodiments, the table may comprise a three or more dimensional look up table, and the look up table may comprises a tier, or level, of the response, for example an alarm.

In some embodiments, the signals may be combined with at least one of adding, subtracting, multiplying, scaling or dividing the at least two of the electrocardiogram signal, the respiration signal or the activity signal. In specific embodiments, the measurement signals can be combined with positive and or negative coefficients determined in response to empirical data measured for a patient population of at least about 100 patients, for example data on about 1000 to 10,000 patients.

In some embodiments, a weighted combination may combine at least two measurement signals to generate an output value according to a formula of the general form $$\text{OUTPUT} = aX + bY$$

where a and b comprise positive or negative coefficients determined from empirical data and X, and Z comprise measured signals for the patient, for example at least two of the electrocardiogram signal, the respiration signal or the activity signal. While two coefficients and two variables are shown, the data may be combined with multiplication and/or division. One or more of the variables may be the inverse of a measured variable.

In some embodiments, the ECG signal comprises a heart rate signal that can be divided by the activity signal. Work in relation to embodiments of the present invention suggest that an increase in heart rate with a decrease in activity can indicate an impending decompensation. The signals can be combined to generate an output value with an equation of the general form $$\text{OUTPUT} = aX/Y + bZ$$

where X comprise a heart rate signal, Y comprises an activity signal and Z comprises a respiration signal, with each of the coefficients determined in response to empirical data as described above.

In some embodiments, the data may be combined with a tiered combination. While many tiered combinations can be used a tiered combination with three measurement signals can be expressed as $$OUTPUT=(\Delta X)+(\Delta Y)+(\Delta Z)$$

where ($\Delta X$), ($\Delta Y$), ($\Delta Z$) may comprise change in heart rate signal from baseline, change in respiration signal from baseline and change in activity signal from baseline, and each may have a value of zero or one, based on the values of the signals. For example if the heart rate increase by 10%, ($\Delta X$) can be assigned a value of 1. If respiration increases by 5%, ($\Delta Y$) can be assigned a value of 1. If activity decreases below 10% of a baseline value ($\Delta Z$) can be assigned a value of 1. When the output signal is three, a flag may be set to trigger an alarm.

In some embodiments, the data may be combined with a logic gated combination. While many logic gated combinations can be used, a logic gated combination with three measurement signals can be expressed as $$OUTPUT=(\Delta X) \text{ AND } (\Delta Y) \text{ AND } (\Delta Z)$$

where ($\Delta X$), ($\Delta Y$), ($\Delta Z$) may comprise change in heart rate signal from baseline, change in respiration signal from baseline and change in activity signal from baseline, and each may have a value of zero or one, based on the values of the signals. For example if the heart rate increase by 10%, ($\Delta X$) can be assigned a value of 1. If respiration increases by 5%, ($\Delta Y$) can be assigned a value of 1. If activity decreases below 10% of a baseline value ($\Delta Z$) can be assigned a value of 1. When each of ($\Delta X$), ($\Delta Y$), ($\Delta Z$) is one, the output signal is one, and a flag may be set to trigger an alarm. If any one of ($\Delta X$), ($\Delta Y$) or ($\Delta Z$) is zero, the output signal is zero and a flag may be set so as not to trigger an alarm. While a specific example with AND gates has been shown the data can be combined in may ways with known gates for example NAND, NOR, OR, NOT, XOR, XNOR gates. In some embodiments, the gated logic may be embodied in a truth table.

The processor system, as described above, performs the methods 500, including many of the steps described above. It should be appreciated that the specific steps illustrated in FIG. 5A provide a particular method of monitoring a patient and responding to a signal event, according to an embodiment of the present invention. Other sequences of steps may also be performed according to alternative embodiments. For example, alternative embodiments of the present invention may perform the steps outlined above in a different order. Moreover, the individual steps illustrated in FIG. 5A may include multiple sub-steps that may be performed in various sequences as appropriate to the individual step. Furthermore, additional steps may be added or removed depending on the particular applications. One of ordinary skill in the art would recognize many variations, modifications, and alternatives.

Experimental Clinical Study

The protocol below has been used to measure signals from actual patients with an adherent device. These data show that an adherent patch as described above can be continuously adhered for at least one week. These data also show that 90 day continuous in home monitoring can be achieved with a set of 13 patches in which one of the patches is replaced each week. The clinical testing device used an adherent device with modifications, as described more fully below and referred to as the MS system (multi-sensor). Although the clinical device did not include wireless circuitry and processor circuitry supported with the patch adhered to the skin of the patient, these data do show that such a device, as described above, can be made by one of ordinary skill in the art based on the teachings described herein. Additional empirical studies can be conducted on a suitable number of patients.

MS Clinical System Description

The MS clinical system includes many of the structure components described above. There is a flexible connection between the electrodes and the flex PCB, for example wires or polyurethane with silver ink. The cover can stretch with the breathable tape on both the clinical device and the above described wireless device. There is generally a gap between the flex PCB and breathable tape in both clinical and above described wireless devices. The tested device used weights to at least partially simulate the weight of wireless and processor circuitry. The adherent device of the MS clinical system comprises four electrodes to measure bioimpedance and ECG signals and a 3-axis accelerometer, as described above. Bioimpedance signals were used to determine patient respiration and patient hydration, and accelerometer signals were used to determine patient activity and posture. The MS clinical adherent patch device comprising the sensors and at least some sensor circuitry were connected to a processor to record data. The processor was connected to the tested adherent device with wires and supported away from the tested adherent patch device, for example around the patient's waist. Data were collected at regular intervals and uploaded to a remote site, as described above.

Clinical testing of the MS clinical system shows the effectiveness of the structures for continuous adherence of at least one week and data collection, and that patches can be successively removed and replaced by the patient for in-home monitoring. This effectiveness has been shown without requiring fully functional electronics circuitry such as a battery, wireless circuitry and process circuitry on the adherent device. For example, the MS system includes an insert with about 20 g of additional weight. Although an insert with a 20 gram weight was used for the MS clinical device, greater amounts of weight and circuitry can be used, for example about 30-50 g. The patch device may be modified to accommodate additional weight, for example by increasing the size of the adherent surface. The shape of the MS clinical patch is generally elongate, similar to the elongate shape shown above.

Study Design and Rationale

The MS System is used in a clinical study of heart failure patients to gather data that can be used to develop an algorithm for diagnosing and predicting impending heart failure decompensation events. Events typically manifest as heart failure-related hospitalization, emergency room or urgent care visits leading to a change in oral or IV diuretic treatment.

The purpose of the clinical study is to correlate physiological signals recorded by the system to clinical events of acute heart failure decompensation (AHFD). Signals from the patch can be weighted and combined to determine an index that associates physiologic parameters to impending events of decompensation. Patients who have been classified as New York Heart Association class III and IV within the last 12 months and have had a recent AHFD event can be enrolled into the study and are monitored with the MS system for approximately 90 days.

AHFD events are defined as any of the following:

1) Any heart failure related ER, Urgent Care, in-office visit or hospitalization requiring administration of IV diuretics, administration of IV inotropes, or ultrafiltration for fluid removal.

2) A change in diuretic, defined as a change in diuretic directed by the health care provider occurring inside a hospital, emergency room, or urgent care setting (i.e. no patient self-directed changes to medications not approved by a health care provider would be included), that satisfies one or more of the following: a) a change in the type of diuretic the patient is taking, b) a dose increase of an existing diuretic, or c) the addition of another diuretic.

3) A heart failure decompensation event for which death is the outcome.

Patients enrolled in the study were asked to replace the patch weekly. The study can enroll at least about 550 patients. The patient was provided with a kit comprising 13 patches for replacement. The patches were placed on alternating left and right sides of the patient's thorax, as described above, to minimize progressive irritation.

The data collected in the study can be used to develop an algorithm to at least one of detect, diagnose or predict an impending cardiac decompensation. The algorithm can be implemented on a processor system as described above. Known methods can be used to analyze the data, for example splitting the patients into two groups, one to develop parameters for the algorithm and a second group to test the algorithm developed with the first group. In many embodiments, the signal of the algorithm may comprise a simple binary output for impending cardiac decompensation of the patient. The logic output, yes or no, can be determined in response to patient data combined as described above. The logic output may comprise a signal, such as a binary Y or N signal.

The developed algorithm can be evaluated with composite sensitivity and false positive patient signal status rates. The sensitivity may be defined as the percent of true positive events out of all condition present events, and the false positive patient status signal status rate can be defined as the number of false positive patient status signals per patient-years of follow up. For example, the sensitivity can be at least 50%, for example at least 60%, at least 70%, or even at least 80%. The false positive patient signal status rate may be limited to no more than about 1.1 false positive patient status signals per patient year, for example no more than about 1.0 false positive patient status signals per patient year, no more than about 0.9 false positive patient status signals per patient year, and even no more than about 0.8 false positive patient status signals per patient year.

Clinical Results

Clinical data are available for the first 180 patients enrolled in the study.

Figure 6A:
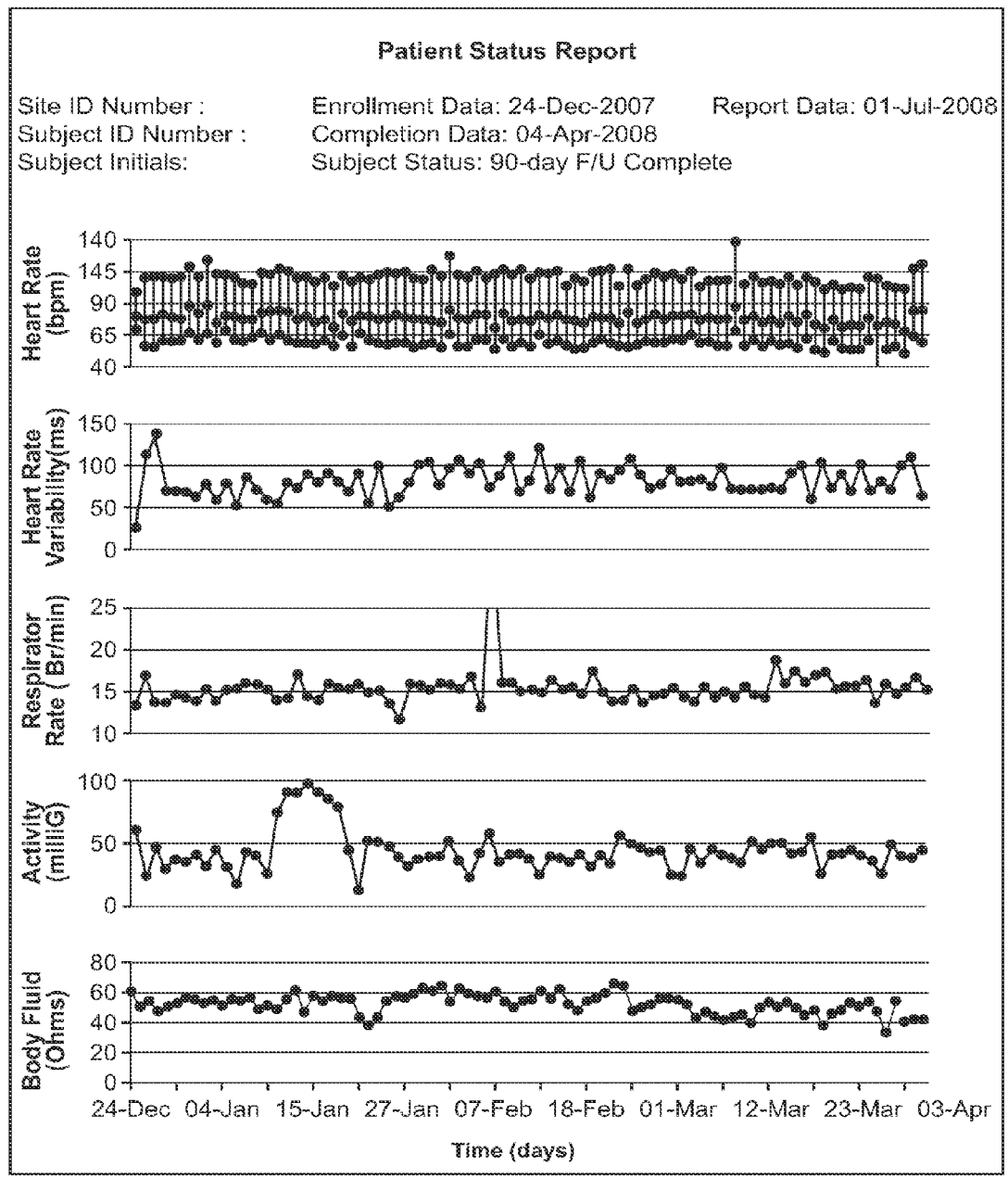
FIGS. 6A and 6B show clinical data measured with an adherent patch device.
Figure 6B:
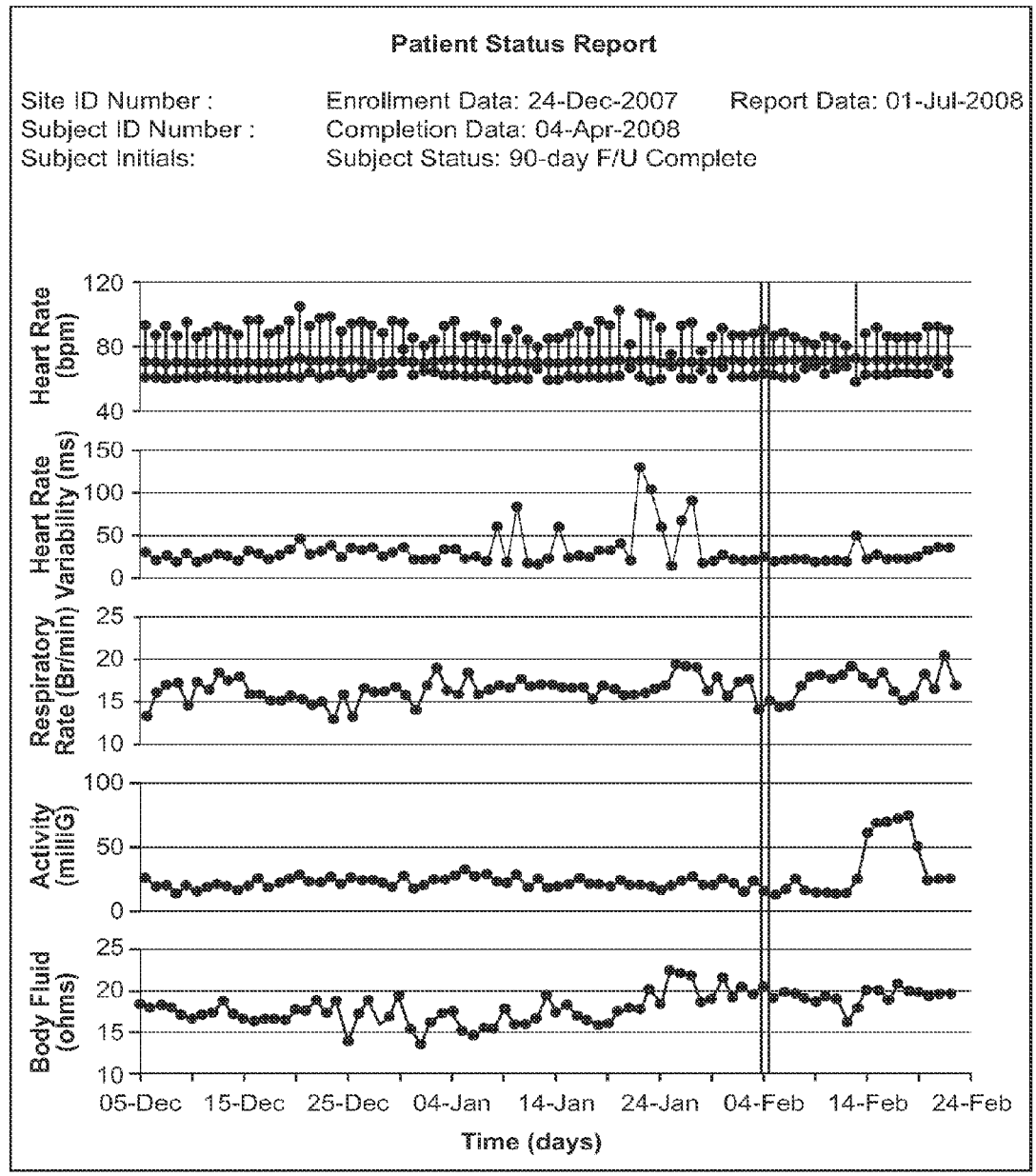

FIGS. 6A and 6B show clinical data measured with an adherent patch device, in accordance with the above protocol. FIG. 6A shows data from a patient with the MS patch adhered to a first patient, and the data was acquired over the 90 day period with the series of 13 patches. The signals measured included Heart Rate (beats per minute), Heart Rate Variability (ms), Respiratory Rate (breaths per minute), Activity (m-G's) and Body Fluid (Ohms) FIG. 6B shows data from a second patient similar to FIG. 6A.

Of the 180 patients who have completed the study with the MS adherent patch, as described above, all patches in all patients adhered continuously without patch failure. In all patients, the first patch adhered continuously for the first week. With the exception of a handful of patient deaths and early withdrawals that were unrelated to device failure, all patients reached the end of 90-day follow-up period having used 13 weekly patches without incident. None of the 180 patients showed skin irritation or damage that required withdrawal from the study.

The above data show that the wireless adherent patch device can be constructed for in home wireless patient monitoring for an extended period of at least 90 day, in which each patch of a set is continuously adhered to a patient for at least one week and each patch is configured to support the measurement circuitry, the processor, the wireless communication circuitry and the battery with the skin of the patient.

While the exemplary embodiments have been described in some detail, by way of example and for clarity of understanding, those of skill in the art will recognize that a variety of modifications, adaptations, and changes may be employed. Hence, the scope of the present invention should be limited solely by the appended claims.

What is claimed is:

1. An adherent device to monitor a patient, the device comprising:
    an adhesive patch configured to adhere to the skin of the patient continuously for at least seven days;
    at least two electrodes connected to the patch and configured to electrically couple to the patient;
    a processor system coupled to the at least two electrodes and configured to monitor a physiologic signal of the patient using the electrodes, wherein the physiologic signal includes an impedance signal related to the hydration of tissue of the patient and wherein the processor is further configured to, based at least in part on the impedance signal measured from the patient, detect an impending cardiac decompensation of the patient; and
    wireless communications circuitry coupled to the processor, wherein the processor is further configured to communicate an alert via the wireless communications circuitry to a remote receiver in response to the detection of the impending cardiac decompensation.

2. The adherent device of claim 1, wherein the processor is further configured to transmit data describing the physiologic signal via the wireless communications circuitry to the remote receiver.

3. The adherent device of claim 1, wherein:
    the physiologic signal is a first physiologic signal;
    the processor system is further configured to monitor a second physiologic signal of the patient; and
    the alert is based on a combination of the first and second physiologic signals.

4. The adherent device of claim 3, wherein the second physiologic signal is monitored using the electrodes.

5. The adherent device of claim 3, wherein the adherent device comprises a microphone, and the second physiologic signal is an audio signal from within the patient detected using the microphone.

6. The adherent device of claim 5, wherein the audio signal includes an S3 heart sound.

7. The adherent device of claim 1, wherein the processor system is further configured to, based at least in part on the physiologic signal measured from the patient:
    calculate a risk of sudden cardiac death of the patient; and
    transmit to the remote receiver via the wireless communications circuitry a report of the risk of sudden cardiac death.

8. The adherent device of claim 7, wherein:
    the processor is further configured to monitor an electrocardiogram (ECG) signal; and
    the risk of sudden cardiac death is calculated based at least in part on an analysis of the ECG signal performed by the processor system.

9. The adherent device of claim 8, wherein the risk of sudden cardiac death is calculated based on recognition by the processor system that the ECG signal indicates one or more conditions selected from the group consisting of pulsus alternans, T-wave alternans, and autonomic imbalance.

10. The adherent device of claim 8, wherein the processor is further configured to continuously monitor a bradycardia of the patient.

11. The adherent device of claim 8, wherein the processor is further configured to recognize that the ECG signal indicates one or more conditions selected from the group consisting of Brugada syndrome with an ST elevation and a short QT interval, and long-QT interval.

12. The adherent device of claim 1, wherein the remote receiver is one of a plurality of remote receivers, and the processor system is configured to select the remote receiver from the plurality of remote receivers based at least in part on the severity of a detected cardiac event.

13. The adherent device of claim 12, wherein the processor system is configured to:
  alert an emergency responder in response to the detection of an event that is immediately life threatening;
  alert a physician in response to the detection of an event that indicates a need for medical care but is not immediately life threatening; and
  alert a family member of the patient or another caregiver in response to the detection of at least one kind of event that is not immediately life threatening and does not indicate a need for medical care.

14. The adherent device of claim 13, wherein the processor system is further configured to alert a monitoring facility in response to the detection of at least one kind of event.

15. The adherent device of claim 1, wherein:
  the processor is configured to monitor an electrocardiogram (ECG) signal;
  the processor is configured to monitor a respiration signal; and
  the processor system is configured to analyze the ECG signal and the respiration signal and to transmit an alert of a life threatening cardiac event upon the detection of an arrhythmia with no respiration.

16. The adherent device of claim 1, wherein:
  the processor is configured to monitor an electrocardiogram (ECG) signal;
  the adherent device further comprises a patient activity sensor that produces a patient activity signal; and
  the processor system is configured to analyze the ECG signal and the patient activity signal and to transmit an alert of a life threatening cardiac event upon the detection of an arrhythmia with no patient activity.

17. The adherent device of claim 1, wherein:
  the processor is configured to monitor an electrocardiogram (ECG) signal;
  the processor system is configured to analyze the ECG signal and to transmit an alert of a life threatening cardiac event upon the detection of one or more events selected from the group consisting of a sustained ventricular tachycardia, a sustained ventricular fibrillation, and an asystole.

18. The adherent device of claim 3, wherein the second physiologic signal is selected from the group consisting of an electrocardiogram signal of the patient, a respiration signal of the patient, and an activity signal of the patient.

19. A method of monitoring a patient, the method comprising:
  adhering an adherent device to the skin of the patient, the adherent device comprising an adhesive patch, at least two electrodes that contact the skin of the patient when the adherent device is adhered to the skin of the patient, a processor system, and wireless communications circuitry;
  monitoring, using the processor system, a physiologic signal of the patient, the physiologic signal being measured using the at least two electrodes, the physiological signal comprising an impedance signal related to the hydration of tissue of the patient;
  detecting, using the processor system, an impending cardiac decompensation of the patient based at least in part on the impedance signal; and
  communicating an alert via the wireless communications circuitry to a remote receiver in response to the detection of the impending cardiac decompensation.

20. The method of claim 19, wherein the adherent device further comprises a microphone, and the method further comprises monitoring an audio signal from within the patient detected using the microphone;
  and wherein detecting the impending cardiac decompensation of the patient comprises detecting the impending cardiac decompensation based at least in part on a combination of the impedance signal and the audio signal.

21. The method of claim 20, wherein the impending cardiac decompensation is detected based at least in part on the recognition of an S3 heart sound in the audio signal.

22. The method of claim 19, further comprising:
  calculating, using the processor, based at least in part on the physiologic signal, a risk of sudden cardiac death of the patient; and
  transmitting to the remote receiver via the wireless communications circuitry a report of the risk of sudden cardiac death.

23. The method of claim 22, wherein the method further comprises:
  monitoring, using the processor system, an electrocardiogram (ECG) signal;
  recognizing, by the processor, in the ECG signal, an indication of at least one condition selected from the group consisting of pulsus alternans, T-wave alternans, and autonomic imbalance; and
  calculating the risk of sudden cardiac death based at least in part on the at least one condition.

24. The method of claim 22, wherein the method further comprises:
  monitoring, using the processor system, an electrocardiogram (ECG) signal; and
  recognizing, by the processor, that the ECG signal indicates one or more conditions selected from the group consisting of Brugada syndrome with an ST elevation and a short QT interval, and long-QT interval.

25. The method of claim 19, further comprising selecting the remote receiver from a plurality of remote receivers according to a tiered response scheme that includes:
  alerting an emergency responder in response to the detection of a cardiac event that is immediately life threatening;
  alerting a physician in response to the detection of a cardiac event that indicates a need for medical care but is not immediately life threatening; and
  alerting a family member of the patient or another caregiver in response to the detection of at least one kind of event that is not immediately life threatening and does not indicate a need for medical care.

26. The method of claim 19, wherein the method further comprises monitoring, by the processor system, an electrocardiogram (ECG) signal, and wherein detecting the impending cardiac decompensation of the patient comprises detecting the impending cardiac decompensation based at least in part on the combination of the physiologic signal and the electrocardiogram signal.

* * * * *